US006204026B1

(12) United States Patent
DesJardin et al.

(10) Patent No.: US 6,204,026 B1
(45) Date of Patent: Mar. 20, 2001

(54) DETECTION OF M. TUBERCULOSIS COMPLEX VIA REVERSE TRANSCRIPTASE SDA

(75) Inventors: Lucy Ellen DesJardin; Mac Donald Cave; Kathleen Davis Eisenach, all of Little Rock, AR (US)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 0 days.

(21) Appl. No.: 08/964,877

(22) Filed: Nov. 5, 1997

(51) Int. Cl.[7] .............................. C12Q 1/68; C07M 21/04
(52) U.S. Cl. ........................... 435/91.2; 435/6; 536/22.1; 536/24.3; 536/24.32
(58) Field of Search .................................. 536/22.1, 24.3, 536/24.32; 435/91.1, 91.2, 6

(56) References Cited

PUBLICATIONS

Matsuo et al. Cloning and expression of the *Mycobacterium bovis* BCG gene for extracellular alpha antigen J. Bacteriology, vol. 170(9). pp. 3847–3854, 1988.*
Jou et al. Single–tube, nested, reverse transcriptase PCR for detection of viable *Mycobacterium tuberculosis*, vol. 35(5), pp. 1161–1165, J. Clinical Microbiology, 1997.*
Douglas F. Moore, et al. Amplification of rRNA for Assessment of Treatment Response of Pulmonary Tuberculosis Patients during AntimicrobialTherapy. Journal of Clinical Microbiology, vol. 34, No. 7, pp. 1745–1749 (Jul. 1996).
A. K. Bej, et al. Detection of viable *Legionella pneumophila* in Water by Polymerase Chain Reaction and Gene Probe Methods. Applied and Environmental Microbiology, vol. 57, No. 2, pp. 597–600 (Feb. 1991).
L. E. DesJardin, et al. Alkaline Decontamination of Sputum Specimens Adversely Affects Stability of Mycobacterial mRNA. vol. 34, No. 10, pp. 2435–2439 (Oct. 1996).
Gabrielle M. E. Van Der Vliet, et al. Assessment of Mycobacterial Viability by RNA Amplification. Antimicrobial Agents and Chemotherapy, vol. 38, No. 9, pp. 1959–1965 (Sep. 1994).
N. Martin–Casabona, et al. Rapid Method for Testing Susceptibility of *Mycobacterium tuberculosis* by Using DNA Probes. Journal of Clinical Microbiology, vol. 35, No. 10, pp. 2521–2525 (Oct. 1997).
Nainn–Tsyr Jou, et al. Single–Tube, Nested Reverse Transcriptase PCR for Detection of Viable *Mycobacterium tuberculosis*. Journal of Clinical Microbiology, vol. 35, No. 5, pp. 1161–1165 (May 1997).
Gerard A. Cangelosi, et al. Detection of Rifampin– and Ciprofoxacin–Resistant *Mycobacterium tuberculosis* by Using Species–Specific Assays for Precursor rRNA. Antimicrobial Agents and Chemotherapy, vol. 40, No. 8, pp. 1790–1795 (Aug. 1996).

Diane E. Kawa, et al. Development of a Rapid Method for Determining the Susceptibility of *Mycobacterium tuberculosis* to Isoniazid Using the Gen–Probe DNA Hybridization System. Anitmicrobial Agents and Chemotherapy, vol. 40, No. 8, pp. 1790–1795 (Aug. 1996).
Tobin J. Hellyer, et al. Strand Displacement Amplification and the Polymerase Chain Reaction for Monitoring Response to Treatment in Patients with Pulmonary Tuberculosis. Antimicrobial Agents and Chemotherapy, vol. 13, pp. 934–941 (1996).
Bharvin K.R. Patel et al. Determination of *Mycobacterium leprae* Viability by Polymerase chain Reaction Amplification of 71–kDa Heat–Shock Protein mRNA. The Journal of Infectious Diseases, vol. 168, pp. 799–800 (1993).
Junko Miyamoto et al. New Drug Susceptibility Test for *Mycobacterium tuberculosis* Using the Hybridization Protection Assay. Journal of clinical Microbiology, vol. 34 No. 5 (1996).
Nainn–Tsyr Jou, et al. Single–Tube, Nested RT–PCR for Detection of Viable *Mycobacterium tuberculosis* and the Rapid Determination of Drug Susceptibility. Advances in Genetic Diagnostics for Infectious Diseases, Abstract (1995).
L. E. DesJardin, et al. Analysis of 85B (alpha antigen) Gene Expression in Patient Sputum Using RT–PCR. 96th General Meeting of the American Society for Microbiology, Abstract U–15 (1996).
L. E. DesJardin, et al. Treatment of Sputum with NaOH and N–acetyl cystein Adversely Affects the Stability of mRNA but not rRNA. 96th General Meeting of the American Society for Microbiology, Abstract U–25 (1996).
L. E. DesJardin, et al. Microbial Markers as Surrogates for Response to Chemotherapy of Tuberculosis. 97th General Meeting American Society for Microbiology, Abstract U–40 (May 1997).
L. E. DesJardin, et al. Microbial Markers as Surrogates for Response to Chemotherapy of Tuberculosis. American Thoracic Society 1997 International Conference, Abstract 117979 (May 1997).

(List continued on next page.)

Primary Examiner—Kenneth R. Horlick
Assistant Examiner—Joyce Tung
(74) Attorney, Agent, or Firm—Benjamin Aaron Adler

(57) ABSTRACT

The present invention provides primers which can be used for *M. tuberculosis* complex-specific detection of α-antigen DNA in a diagnostic assay performed on clinical specimens or in a culture-confirmation assay following growth of the organism in vitro. These primers and probes can also be employed in a reverse transcriptase-mediated amplification system for *M. tuberculosis* complex α-antigen mRNA. Such an assay provides a means by which to determine the viability of *M. tuberculosis* complex organisms either in clinical specimens or when grown in culture. Also described are methods for the detection of the products of amplification with a radiolabeled probe by chemiluminescent assay or fluorescence polarization analysis.

11 Claims, 12 Drawing Sheets

PUBLICATIONS

Tobin J. Hellyer, et al. Determination of Drug Resistance in *Mycobacterium tuberculosis* by Quantitative Reverse Transcriptase–PCR Using the ASI Prism 7700. ASM Conference on Tuberculosis: Past, Present, and Future, Abstract B–10 (Jul. 1997).

L. E. DesJardin, et al. Use of competitive PCR and the AB 7700 for Monitoring Microbial Load in Patients during Chemotherapy. ASM Conference on Tuberculosis: Past, Present, and Future, Abstract B–14 (Jul. 1997).

L. E. DesJardin, et al. Measurement of Microbial mRNA in Sputum from Patients on Standard Tuberculosis Chemotherapy. ASM Conference on Tuberculosis: Past, Present, and Future, Abstract B–15 (Jul. 1997).

L. E. DesJardin, et al. Microbial Markers as Surrogates for Response to Chemotherapy of Tuberculosis. Thirty–Second U.S.–Japan Cooperative Medical Science Program Tuberculosis–Leprosy Research Conference, Poster 3 (Jul. 1997).

* cited by examiner

```
ATGACAGACGTGAGCCGAAAGATTCGAGCTTGGGACGCGATTGATGATCGGCACGGCAGCGGCTGTAGTCCTTCCGGGCTTGTGGGGCTTGCCGGCG
          |         |         |         |         |         |         |         |         |         |
                                                                                                    100
TACTGTCTGCACTCGGCTTTCTAAGCTCGAACCCCTGCGGCTAACTACTAGCCGTCGCCGTCGCCGACATCAGGAAGGCCGGACCACCCCGAACGGCCGC
          |         |         |         |         |         |         |         |         |         |
                                                                                                    200
GAGCGGCAACCGCGGGGCGCGTTCTCCCGGCTGCCGGTCGCAGGTACCCTGCGAGTACCTGCCGTCGCCGACATGGCCCGACATCAAGGTTCAGTTCCA
          |         |         |         |         |         |         |         |         |         |
                                                                                                    300
CTCGCCGTTGGCGCCCGCGCAAGAGGGCCGGCCCCAGCTCATGGACGTCCACGGCAGCAGCCTACCCGGCGCTGTAGTTCCAAGTCAAGGT
          |         |         |         |         |         |         |         |         |
GAGCGGTGGGAACAACTCACCTGCGGTTTATCTGCTGGGATATCAACACCCCGGCGTTCGAGTGG
          |         |         |         |         |         |         |         |         |         |
                                                                                                    400
CTCGCCACCCTTGTTGAGTGGACGCCAAATAGACGAGCTGCCGGACGCGGGTTCTGCTGATGTTGCCGACCTATAGTTGTGGGGCCTGCAAGCTCACC
          |         |         |         |         |         |         |         |         |         |
TACTACCAGTCGGGACTGTCGATAGTCATGCCGGTCCAGCTTCTACAGCGACTGGTACAGCCCGGCCTGCGGTAAGGCTGGCTGCCAGA
          |         |         |         |         |         |         |         |         |         |
                                                                                                    500
ATGATGGTCAGCCCTGACACGGCTATCAGTACGGCCAGCTGCCAGCTCAGGTCCAGGTCAGGATGTGCTGACCATGTCGGACCGACGGTCT
          |         |         |         |         |         |         |         |         |
CTTACAAGTGGGAAACCTTCCTGACCAGCAGCTGCCGAGCTGCCGGCCGTGAAGCCGTGAAGCCCAACAGGGCCGGACCGCTGCAATCGGCTTGTCGAT
          |         |         |         |         |         |         |         |         |
GAATGTTCACCCTTTGGAAGGACTTCGCTCGACACGGGTTACCAACAGGGGTTGTCCCGGCACTTCGGGTGGCCGTCGCCGACGTTAGCCGAACAGCTA
```

Seq ID #4 → | Seq ID #15 → | Seq ID #8 → | Seq ID #9 → | Seq ID #16, 17 →
← Seq ID #10

B, biotin; AP, alkaline phosphatase

```
  1  ACCTTCCTGACCAGCGAGCTGCCCGCAATGGTTGTCCGCCA  Mtb Target
  1  ACCTTCCTGACCAGCGAGCTGCCCGCAATGGTTGTCCGCCA  Control 41  ACAGGGCCGTGAAGCCCACCCGGCAGCGCTGCAATCGGCTT  Mtb Target
 41  ACAGGGGTGAGCAC GCCCACCCGGCAGCGCTGCAATCGGCTT  Control 81  GTCGATGGCCCGGCTCGTCGGCAATGATCT  Seq ID #22
 81  GTCGATGGCCCGGCTCGTCGGCAATGATCT  Seq ID #23
```

FIG. 6B

DETECTION OF M. TUBERCULOSIS COMPLEX VIA REVERSE TRANSCRIPTASE SDA

FEDERAL FUNDING LEGEND

This invention was produced in part using funds obtained through a grant from the National Institutes of Health. Consequently, the federal government has certain rights in this invention.

BACKGROUND OF THE INVENTION

1. Field of the Invention

The present invention relates generally to the field of clinical microbiology. Specifically, the present invention relates to the detection of viable organisms of the *Mycobacterium tuberculosis* complex using a reverse transcriptase polymerase chain reaction assay.

2. Description of the Related Art

The resurgence of tuberculosis in the United States over the past decade and its continued worldwide dominance as a cause of morbidity and mortality (Raviglione et al, 1995) have focused attention on the need for more rapid and reliable means of diagnosis. Traditionally, diagnosis is dependent upon acid-fast staining and culture of the causative agent, *Mycobacterium tuberculosis* (*M. tuberculosis*), in broth or on solid media. However, this process may require up to 6 weeks owing to the slow growth rate of the organism. In contrast, nucleic acid amplification assays have the potential to reduce the time for definitive diagnosis to as little as one day. Several assays have been described for the detection of nucleic acid sequences that are specific for the *M. tuberculosis* complex which comprises *M. tuberculosis*, *M. bovis*, *M. bovis bacille* Calmette-Guérin (BCG), *M. africanum* and *M. microti* (Eisenach et al, 1991; Iovannisci et al, 1993; Jonas et al, 1993; Shah et al, 1995; van der Vliet et al, 1993; Walker et al, 1992). Although beneficial to the initial diagnosis of infection, such assays have so far proven unsuitable for monitoring the response of patients to therapy.

Typically, successful treatment of a patient with tuberculosis results in conversion of smears and cultures to negative within 3–4 months. However, recently it has been demonstrated that DNA-based amplification assays such as the Polymerase Chain Reaction (PCR), Ligase Chain Reaction (LCR) and Strand Displacement Amplification (SDA) are an inappropriate substitute for conventional microbiological methods of patient follow-up since *M. tuberculosis* DNA may persist for long periods after smears and cultures have become negative (Hellyer et al, 1996). Similarly, a poor correlation has been observed between smear and culture results and those obtained with the Gen-Probe Amplified *Mycobacterium Tuberculosis* Direct Test for *M. tuberculosis* 16S ribosomal RNA (Moore et al, 1996).

In prokaryotic cells, messenger RNA (mRNA) is degraded rapidly with a typical half-life of 3 min (Belasco et al, 1986; von Gabain et al, 1983). Consequently an mRNA-based amplification assay is likely to detect only living organisms and thus be a good indicator of therapeutic efficacy. Thus, the prior art is deficient in methods for diagnosis of and determination of efficacy of treatment for *M. tuberculosis*. The present invention fulfills this long-standing need and desire in the art.

SUMMARY OF THE INVENTION

The present invention provides a reverse transcriptase-mediated polymerase chain reaction assay (RT-PCR) for *M. tuberculosis* α-antigen mRNA (also termed the US-Japan antigen 6 or the 30 kd, 85B or MPB59 protein). This target was selected because the α-antigen is one of the most abundant proteins produced by *M. tuberculosis* in broth cultures as well as in human mononuclear phagocytes (Lee et al, 1995; Harth et al, 1996). α-antigen may comprise up to 41% of protein in culture supernatants (Wiker et al., 1992) and it is reasonable to expect viable cells to possess a corresponding abundance of the encoding mRNA.

The present invention provides specifically a reverse transcriptase-mediated polymerase chain reaction (RT-PCR) assay for *M. tuberculosis* α-antigen using primers selected from sequences disclosed in Table 1. A preferred embodiment comprises a method for the detection of viable organisms of the *M. tuberculosis* complex by RT-PCR in clinical specimens or in vitro cultures, comprising the steps of: adding mRNA isolated from the specimens or cultures to an appropriate buffer containing a primer, nucleotides and a reverse transcriptase enzyme to form a reaction mixture; incubating the reaction mixture at a suitable temperature to permit synthesis of EDNA by the reverse transcriptase; transfering an aliquot of said cDNA to a suitable buffer containing one or more additional primers, nucleotides and a DNA polymerase to form a PCR reaction mixture; incubating the PCR mixture over successive cycles of heating and cooling to facilitate generation of specific products by the DNA polymerase; and detecting the products by gel electrophoresis, autoradiography or emission of fluorescence, wherein a presence of said products indicates the presence of viable *M. tuberculosis* complex organisms and an absence of said products indicates an absence of said viable *M. tuberculosis* complex organisms in said sample.

A preferred embodiment is to perform the method wherein the sequence of the primer for reverse transcription is SEQ ID No. 13, and wherein the sequences of the primers used for PCR amplification of the cDNA are SEQ ID No. 12 and SEQ ID No. 13, and wherein the products are detected by incorporation of radiolabeled SEQ ID No. 12 and SEQ ID No. 13 in said reaction mixture, followed by gel electrophoresis of the products of the reaction and autoradiography. A particularly preferred embodiment of the objective is to detect the products using a fluorescently-labeled probe wherein the sequence of said probe is SEQ ID No. 14 and wherein the PCR amplification is performed using a 5' fluorogenic exonuclease assay (Holland et al, 1991; Livak et al, 1995).

Other and further aspects, features, and advantages of the present invention will be apparent from the following description of the presently preferred embodiments of the invention. These embodiments are given for the purpose of disclosure.

BRIEF DESCRIPTION OF THE DRAWINGS

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

FIG. 1 shows diagrammatically the positions of the primer sequences recited in Table 1 within the *M. tuberculosis* α-antigen gene. The sequences diagrammatically shown in SEQ ID Nos. 15–17 represent the 3'-terminus homologous oligonucleotide region of the SDA primers corresponding to SEQ ID Nos. 1–3, respectively.

FIG. 6B shows the alignment of nucleotides 415–497 of the *M. tuberculosis* α-antigen gene (DeWit et al., 1994) and the internal control sequence which was cloned into the plasmid vector pSP64 Poly(A). Boxed residues are those that differ from the native *M. tuberculosis* sequence.

DETAILED DESCRIPTION OF THE INVENTION

Figure 2:
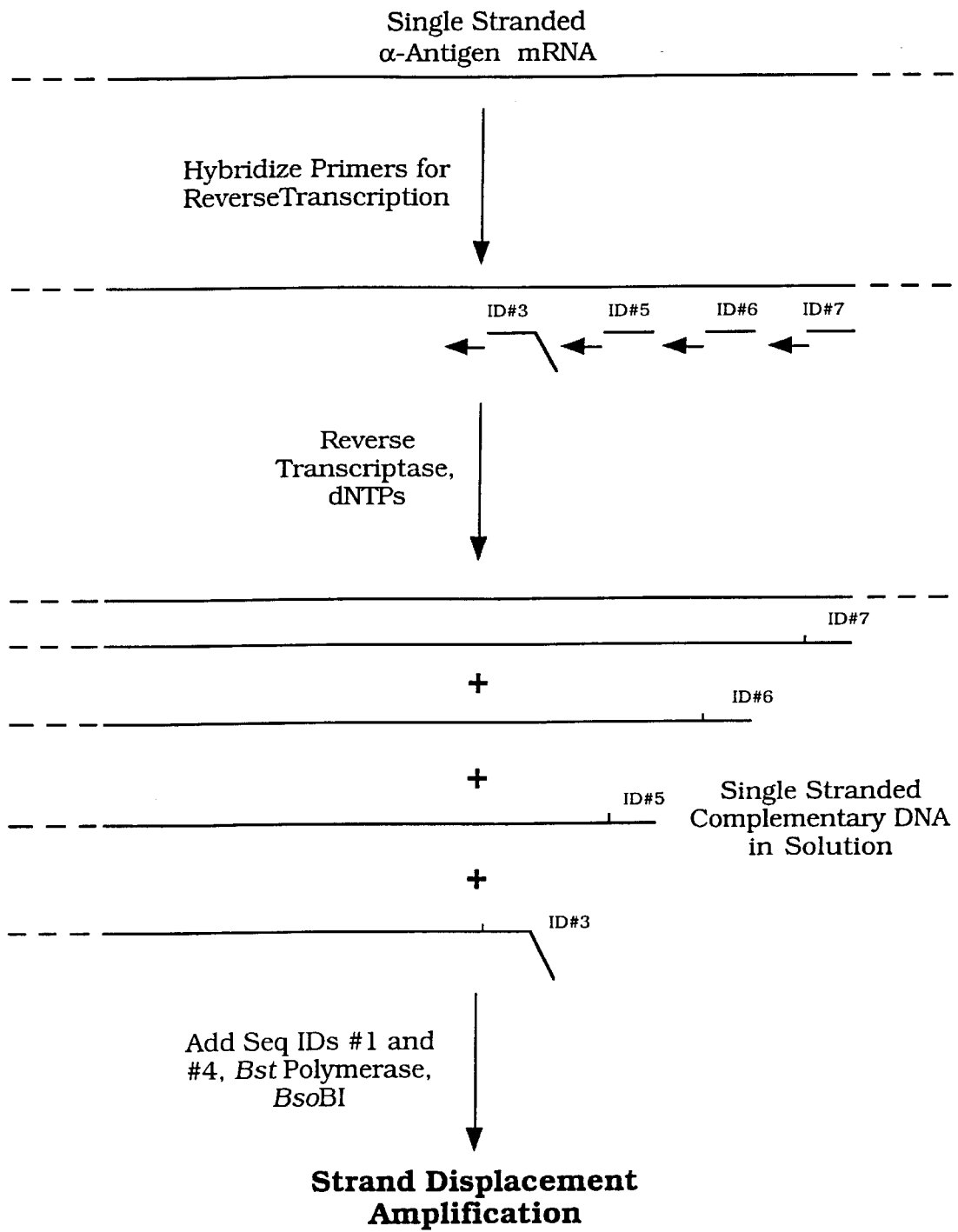
FIG. 2 is a schematic diagram showing the products of reverse transcription of *M. tuberculosis* α-antigen mRNA.

It will be apparent to one skilled in the art that various substitutions and modifications may be made to the invention disclosed herein without departing from the scope and spirit of the invention.

As used herein the term "tuberculosis" shall mean any human or animal infection caused by an organism belonging to the *M. tuberculosis* complex.

As used herein, the term "strand displacement amplification" or "SDA" shall mean the isothermal amplification of DNA through the activity of a restriction enzyme and DNA polymerase.

As used herein, the term "reverse transcriptase strand displacement amplification" or "RT-SDA" shall mean strand displacement amplification of complementary DNA generated by copying an RNA template into DNA using an enzyme with reverse transcriptase activity.

As used herein, the term "*M. tuberculosis* complex" shall mean organisms belonging to the species *Mycobacterium tuberculosis*, *Mycobacterium africanum*, *Mycobacterium microti* and *Mycobacterium bovis*, including organisms of the sub-species *Mycobacterium bovis* bacille Calmette-Guérin (BCG).

As used herein, the term "α-antigen" shall mean the mycobacterial protein of approximately 30 kd also commonly termed the 30 kd antigen, antigen 85B, US-Japan antigen 6 and MPB59 protein. The protein is encoded in the *M. tuberculosis* complex by a gene of approximately 1 kb in length, as described by Matsuo et al (1988) and De Wit et al (1994) (GenBank accession numbers M21839 and X62398).

As used herein, the term "complex-specific detection" shall mean the detection of the products of DNA or RNA amplification which possess a base sequence that is unique to a defined group of closely-related organisms.

As used herein the term "polymerase chain reaction" or PCR shall mean the amplification of DNA through the cyclical raising and lowering of temperature and the activity of a thermostable DNA polymerase.

As used herein the term "5' fluorogenic exonuclease assay" shall mean a method which uses the 5' to 3' exonuclease activity of a DNA polymerase enzyme to generate fluorescence during a nucleic acid amplification reaction.

As used herein the term "Applied BioSystems Prism 7700 Sequence Detection System" shall mean an instrument used to perform quantitative 5' fluorogenic exonuclease PCR amplification assays.

In accordance with the present invention there may be employed conventional molecular biology, microbiology, and recombinant DNA techniques within the skill of the art. Such techniques are explained fully in the literature; see, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells And Enzymes"

(IRL Press, (1986)); B. Perbal, "A Practical Guide To Molecular Cloning" (1984).

Therefore, if appearing herein, the following terms shall have the definitions set out below.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

As used herein the term "gene" shall mean a region of DNA encoding a polypeptide chain.

As used herein the term "messenger RNA" or "mRNA" shall mean an RNA molecule that encodes for one or more polypeptides.

As used herein the term "DNA polymerase" shall mean an enzyme which catalyzes the polymerization of deoxyribonucleotide triphosphates to make DNA chains using a DNA template.

As used herein the term "reverse transcriptase" shall mean an enzyme which catalyzes the polymerization of deoxy- or ribonucleotide triphosphates to make DNA or RNA chains using an RNA or DNA template.

As used herein the term "complementary DNA" or "cDNA" shall mean the DNA molecule synthesized by polymerization of deoxyribonucleotides by an enzyme with reverse transcriptase activity.

As used herein the term "base" shall mean a structure of carbon, nitrogen and hydrogen which is a constituent of DNA and RNA.

As used herein the term "viable" or "active" shall mean bacterial cells which are capable of replication either in vivo in a suitable host or in vitro when supplied with appropriate nutrients.

The term "oligonucleotide", as used herein in referring to the probes or primers of the present invention, is defined as a molecule comprised of two or more deoxy- or ribonucleotides, preferably more than ten. Its exact size will depend upon many factors which, in turn, depend upon the ultimate function and use of the oligonucleotide.

The term "primer" as used herein refers to an oligonucleotide, whether occurring naturally or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, the source of primer and the method used. For example, for diagnostic applications, depending on the complexity of the target sequence, the oligonucleotide primer typically contains 10–25 or more nucleotides, although it may contain fewer nucleotides.

As used herein the term "strand displacement amplification primer" or "SDA primer" shall mean an oligonucleotide with substantial complementarity at its 3'-terminus to another DNA or RNA sequence, a non-complementary 5'-tail of unspecified length or composition but which includes within this region a recognition sequence for a restriction endonuclease.

As used herein the term "bumper primer" shall mean an oligonucleotide of unspecified length which possesses substantial complementarity with a DNA sequence which is located 5' to the complementary sequence of an adjacent SDA primer.

As used herein the term "detector primer" shall mean an oligonucleotide of unspecified length which possesses substantial complementarity to the DNA or RNA products generated in a strand displacement or other amplification assay.

As used herein the term "capture primer" shall mean an oligonucleotide of unspecified length with substantial complementarity to a specific DNA or RNA molecule.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein the term "hybridization" refers generally to a technique wherein denatured RNA or DNA is combined with complementary nucleic acid sequence which is either free in solution or bound to a solid phase. As recognized by one skilled in the art, complete complementarity between the two nucleic acid sequences is not a pre-requisite for hybridization to occur. The technique is ubiquitous in molecular genetics and its use centers around the identification of particular DNA or RNA sequences within complex mixtures of nucleic acids.

As used herein, the terms "restriction endonucleases" and "restriction enzymes" refer to bacterial enzymes which cut double-stranded DNA at or near a specific nucleotide sequence.

The present invention is directed to providing a method for determining the presence or absence of *Mycobacterium tuberculosis* complex. The objective of the present invention is to provide a reverse transcriptase-mediated polymerase chain reaction (RT-PCR) assay for detection of viable organisms of the *M. tuberculosis* complex. Primers selected from sequences disclosed in Table 1 may be used to attain this objective. A particular embodiment comprises the steps of: adding mRNA isolated from the samples to an appropriate buffer containing a primer, nucleotides and a reverse transcriptase enzyme to form a reaction mixture; incubating the reaction mixture at a suitable temperature to permit synthesis of cDNA by the reverse transcriptase; transfering an aliquot of the cDNA to a suitable buffer containing one or more additional primers, nucleotides and a DNA polymerase; incubating this mixture over successive cycles of heating and cooling to facilitate generation of specific PCR products by the DNA polymerase; detection of the products, wherein a presence of the products indicates the presence of viable M. tuberculosis complex organisms in the sample and an absence of the products indicates an absence of the organisms in the sample.

The following examples are given for the purpose of illustrating various embodiments of the invention and are not meant to limit the present invention in any fashion:

EXAMPLE 1

Identification of Primers and Probes for SDA of M. tuberculosis α-antigen

Figure 1B:
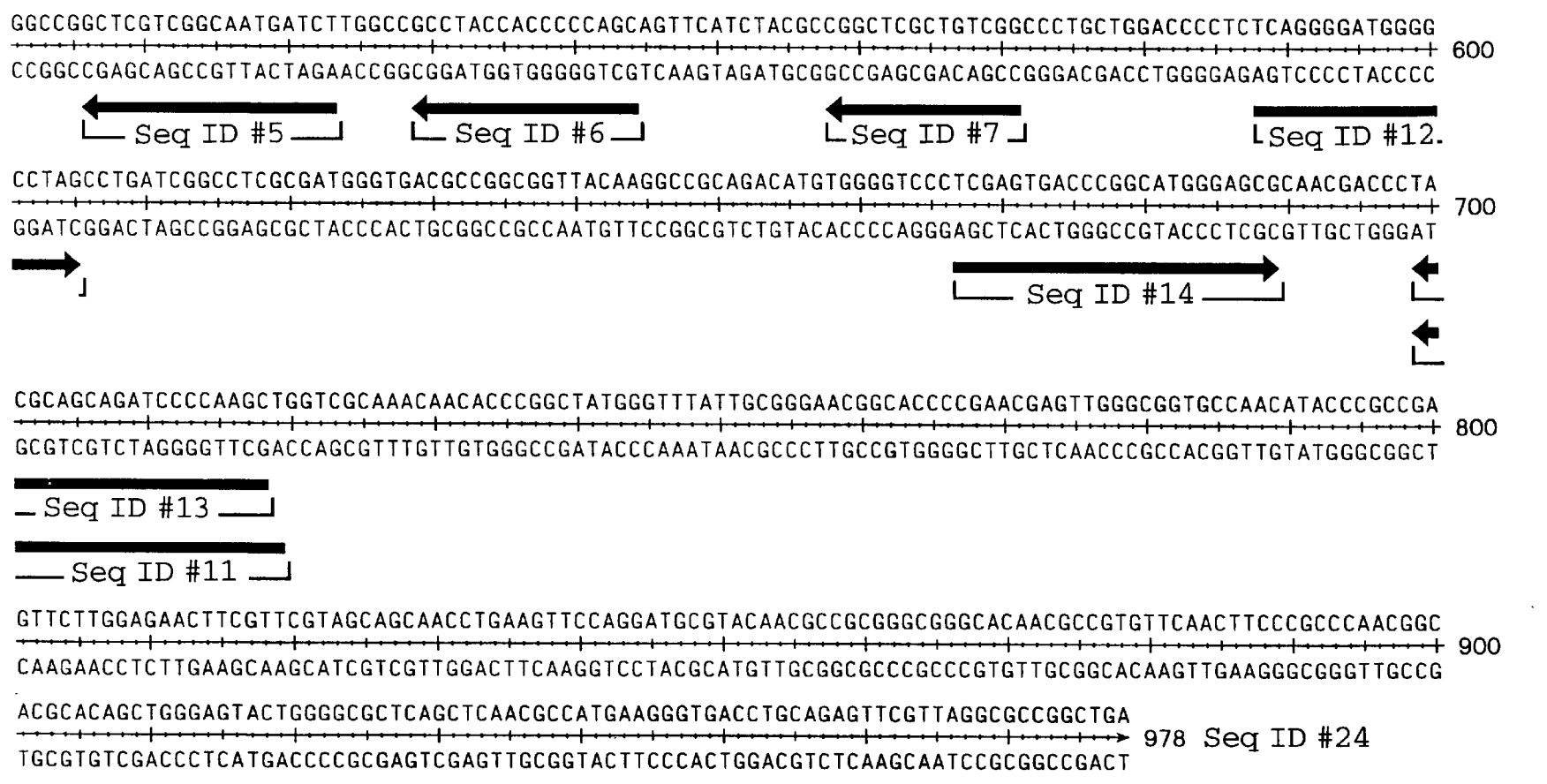

Primers were based on published sequences of the α-antigen genes from M. tuberculosis strain Erdman, M. bovis strain 1173P2 (De Wit et al, 1994) and M. bovis BCG strain Tokyo (Matsuo et al, 1988). Computer-assisted alignment was carried out with the α-antigen gene sequences of M. avium (Ohara et al, 1993), M. intracellulare (Kitaura et al, 1993), M. scrofulaceum (Takano et al, 1994), M. kansasii (Matsuo et al, 1990) and M. leprae (De Lima et al, 1991). Primer sequences are listed in Table 1 and their positions within the M. tuberculosis α-antigen gene are shown diagrammatically in FIG. 1. The sequences diagrammatically shown in SEQ ID Nos. 15–17 represent the 3'-terminus homologous oligonucleotide region of the SDA primers corresponding to SEQ ID Nos. 1–3, respectively.

In Table 1, BsoBI recognition sequences are in bold face. SDA primer target binding regions are underlined. 5'-fluoresceinated Seq ID No. 8 is used in fluorescence polarization analysis of strand displacement amplified DNA or mRNA target. (B, biotin; AP, alkaline phosphatase).

Seq ID Nos. 1–No. 3 are SDA primers consisting of a target binding region, recognition site for the restriction enzyme BsoBI and additional 5' nucleotides. Seq ID No. I is a sense primer from nt 445–459 while Seq ID Nos. 2 and 3 are antisense primers from nt 497–482. Seq ID Nos. 2 and 3 are identical except for the inclusion of two extra T residues in the tail region of Seq ID No. 3 to destabilize a hairpin structure formed between the target binding region and the BsoBI recognition site. Primer Seq ID No. 3 was shown to provide greater amplification efficiency than Seq ID No. 2 in SDA of M. tuberculosis α-antigen DNA. Seq ID Nos. 4–7 are bumper primers required for target generation during the first cycle of SDA. Seq ID No. 4 is a sense primer spanning nt 415–432 while Seq ID No. 5, No. 6 and No. 7 are antisense primers spanning nt regions 523–506, 544–529 and 571–558 respectively. Seq ID No. 8 is the detector probe used for primer extension analysis of the amplification products and corresponds to nt 481–462 of the antisense strand. Fluorescein-labeled Seq ID No. 8 can also be used in a fluorescence polarization-based detection assay (Walker et al, 1996) for either α-antigen DNA or mRNA. Seq ID No. 9 and No. 10, respectively, are the capture and detector probes used in chemiluminescent detection of SDA-amplified products (Spargo et al, 1993) and correspond to nt 469–457 and 481–470 of the antisense DNA strand. Seq ID No. 11 is an antisense primer spanning nt 719–699 and is designed as a specific capture probe for the recovery of α-antigen mRNA from complex solutions including clinical specimens. Seq ID No. 11 was designed to span a region of the M. tuberculosis complex α-antigen gene which differs extensively from that of other mycobacteria with the aim of providing an additional level of target specificity above that achieved with the SDA primers (Seq ID Nos. 1–3) alone.

Seq ID No. 2, No. 3 and Nos. 5–7 were designed to take advantage of the strand displacement activity of avian myeloblastosis virus (AMV) reverse transcriptase in copying α-antigen mRNA to complementary DNA (cDNA). cDNA synthesis can be achieved using a single primer, however, the strand displacement activity of AMV reverse transcriptase (Collett et al, 1980) can be exploited to generate additional cDNA copies which in turn become the target for amplification in SDA (FIG. 2). Amplification efficiency was increased 1.5–2-fold by inclusion of bumper primers Seq ID No. 6 and Seq ID No. 7 in the reverse transcription reaction in addition to bumper primer Seq ID No. 5 and SDA primers Seq ID No. 2 or Seq ID No. 3.

TABLE 1

M. tuberculosis Alpha Antigen Primer Sequences

| | 5'-3'Sequence | Position |
|---|---|---|
| SDA Primers | | |
| Seq ID No. 1: | CgA TTC CgC TCC AgA CTT CTC ggg TTT gTC CgC CAA CAg g | 445–459 |
| Seq ID No. 2: | ACC gCA TCg AgT ACA TgT CTC ggg TgA CAA gCC gAT TgC Ag | 497–482 |
| Seq ID No. 3: | ACC gCA TCg AgT ACA TgT CTC ggg TTT gAC AAg CCg ATT gCA g | 497–482 |
| Bumper Primers | | |
| Seq ID No. 4: | ACC TTC CTg ACC AgC gAg | 415–432 |
| Seq ID No. 5: | AgA TCA TTg CCg ACg AgC | 523–506 |
| Seq ID No. 6: | gCT ggg ggT ggT Agg C | 544–529 |
| Seq ID No. 7: | CCg ACA gCg AgC Cg | 571–558 |
| SDA Detector Primer | | |
| Seq ID No. 8 | CgC TgC Cgg Tgg gCT TCA Cg | 481–462 |

TABLE 1-continued

| *M. tuberculosis* Alpha Antigen Primer Sequences | | |
|---|---|---|
| | 5'-3'Sequence | Position |
| Primers for Chemiluminescent Detection of *M. tuberculosis* | | |
| Seq ID No. 9 | gCT TCA Cgg CCC T-(BBB) | 469–457 |
| Seq ID No. 10 | CgC TgC Cgg Tgg-(AP) | 481–470 |
| Capture Probe for Isolation of α-antigen mRNA: | | |
| Seq ID No. 11 | AgC TTg ggg ATC TgC TgC gTA-(B) | 719–699 |
| PCR Primers | | |
| SEQ ID No. 12 | TCA ggg gAT ggg gCC Tag | 588–605 |
| SEQ ID No. 13 | gCT Tgg ggA TCT gCT gCg TA | 718–699 |
| PCR Detector Primer: | | |
| SEQ ID No. 14 | TCg AgT gAC CCg gCA Tgg gAg Cg | 667–689 |

EXAMPLE 2

Strand Displacement Amplification of *M. tuberculosis* α-antigen DNA

The following amplification conditions were used in an initial screen to determine sensitivity and specificity. Thermophilic SDA reactions were performed in 50 μl volumes. Target DNA was added to buffer containing (final concentrations) 55 mM $K_iPO_4$, 10% dimethyl sulfoxide, 8% glycerol (including ~4% from subsequent addition of the enzymes), 500 nM SDA primers, 50 nM bumper primers (Seq ID No. 4 and Seq ID No. 5), 0.8 mM 2' deoxycytidine 5'-O-(thiotriphosphate), 0.2 mM dATP, dGTP and dUTP, 500 ng human placental DNA (Sigma), and 5 μg acetylated bovine serum albumin. Tubes were heated at 95° C. for 2.5 min to denature the target DNA and were equilibrated for 3 min at 50° C. prior to addition of 1 U uracil DNA glycosylase (UDG). Incubation was continued for 10 min before addition of 120 U BsoBl, 20 U Bst polymerase (both New England BioLabs), 4 U UDG inhibitor and 7 mM magnesium acetate (final concentration). Incubation was continued for 45 min more and reactions were stopped by heating for 3 min at 95° C. The products of SDA were detected by autoradiography following primer extension with $^{32}P$-labeled probe (Seq ID No. 8) and electrophoretic separation in denaturing polyacrylamide gels.

The SDA primer combination Seq ID No. 1 and Seq ID No. 3 was found to give better amplification efficiency than could be achieved under the same conditions with Seq ID No. 1 and Seq ID No. 2. The analytical sensitivity of this system using the Seq ID No. 1, Seq ID No. 3 SDA primer pair was shown to be approximately 50 genome equivalents of *M. tuberculosis* DNA. Twenty-four isolates of *M. tuberculosis* from North and South America, Asia, Africa, and Europe were tested in SDA using Seq ID No. 1, No. 3, No. 4 and No. 5. All yielded specific products by primer extension analysis with Seq ID No. 8, as did four North American isolates of *M. bovis* (including two of human origin), *M. bovis* BCG (Glaxo strain) and one strain each of *M. africanum* and *M. microti.* Included in this panel of *M. tuberculosis* complex organisms was one IS6110-negative isolate that cannot be detected by existing SDA systems which utilize this element as a specific target for amplification (Walker, et al., 1992).

The Seq ID Nos. 1, 3, 4 and 5 primer set was also tested for cross reactivity with other species of mycobacteria. No significant cross-reaction was observed among 36 strains of non-tuberculous mycobacteria comprising 10 isolates of *M. avium—M. intracellulare,* seven of *M. fortuitum,* five of *M. xenopi,* four of *M. malmoense,* three of *M. kansasii,* three of *M. chelonei* and one each of *M. scrofulaceum, M. gordonae, M. abscessus* and *M. celatum.* Similarly, no cross-reaction was detected with the phylogenetically-related organisms *Actinomyces israeli, Corynebacterium diphtheriae, Nocardia braziliensis, Rhodococcus rhodocrous* and *Streptomyces albus.*

The conditions for amplification of *M. tuberculosis* complex α-antigen DNA have been optimized subsequently in order to increase the analytical sensitivity and reproducibility of the assay. This modified system has a reproducible analytical sensitivity of 10 copies of α-antigen target DNA and is performed in 50 μl volumes as follows: Target DNA was added to buffer containing (final concentrations) 52.5 mM $K_iPO_4$, 12% dimethyl sulfoxide, 7.7% glycerol (including 3% from subsequent addition of enzymes), 500 nM SDA primers (Seq ID No. 1 and No. 3), 50 nM bumper primers (Seq ID No. 4 and No. 5), 0.8 mM $dC_STP$, 0.2 mM dATP, dGTP and dUTP, 500 ng human placental DNA (Sigma), and 5 μg acetylated bovine serum albumin. Tubes were heated at 95° C. for 2.5 min to denature the target DNA and equilibrated for 3 min at 45° C. prior to addition of 1 U uracil DNA glycosylase (UDG). Incubation was continued for 10 min at 45° C. before the tubes were re-equilibrated at 52.5° C. for 3 min and 40 U BsoBI, 15 U Bst polymerase (both New England BioLabs), 4 U UDG inhibitor and 7 mM magnesium acetate (final concentration) were added. Amplification was carried out for 45 min and reactions were stopped by heating for 3 min at 95° C. The products of amplification can be detected by primer extension analysis with radiolabeled Seq ID No. 8 or by chemiluminescent assay using Seq ID No. 9 and Seq ID No. 10 (see Example 5 below).

EXAMPLE 3

Reverse Transcriptase-SDA of *M. tuberculosis* α-antigen mRNA

The above SDA system for *M. tuberculosis* α-antigen DNA provided the basis for the development of a reverse transcriptase-mediated assay for detection of the α-antigen mRNA. Conditions for the reverse transcription (RT) reaction were optimized using in vitro mRNA transcripts generated from a partial clone of the α-antigen gene of *M. tuberculosis* H37R$_V$ in *Escherichia coli* (Ying et al, 1995). This clone comprised a 600-base pair fragment, which encompassed the SDA target region ligated into the EcoRV and SacII sites of pBlueScript KS+ (Stratagene). In vitro transcripts were generated from the T3 RNA polymerase promoter using an Ambion MEGAscript™ T3 Kit according to the manufacturer's instructions.

RT reactions were performed in 20 µl volumes. Target mRNA was added to buffer containing (final concentrations) 30 mM K$_3$PO$_4$, 10% DMSO, 1250 nM Seq ID No. 3, 125 nM Seq ID No. 5, 12.5 nM Seq ID No. 6, 1.25 nM Seq ID No. 7, 0.8 mM dC$_S$TP, 0.2 mM dATP, dGTP and dUTP, 2 mM magnesium acetate, 300 ng human placental DNA, 5 µg BSA, 1 U UDG and 1 U Prime RNase Inhibitor™ (5 Prime-3 Prime, Inc.). Reaction mixtures were incubated at 50° C. for 15 min to facilitate removal of contaminating amplicons by the UDG enzyme before addition of 4 U UDG inhibitor and 2.5 U AMV reverse transcriptase (Boehringer Mannheim). Reverse transcription was carried out for 15 min at 50° C. SDA was then initiated at the same temperature in a final volume of 50 µl through addition to the concentrations listed above for DNA amplification of K$_i$PO$_4$, DMSO, Seq ID No. 1 and Seq ID No. 4, dC$_S$TP, dUTP, dATP, dGTP, human placental DNA, magnesium acetate, BsoBI and Bst polymerase. Incubation was continued for 45 min before reactions were stopped by heating at 95° C. for 3 min. The products of SDA were detected by autoradiography following primer extension with $^{32}$P-labeled Seq ID No. 8 and electrophoretic separation in denaturing polyacrylamide gels.

This system has an analytical sensitivity in the order of 10–50 in vitro transcripts. Amplification efficiency was increased 1.5–2-fold by inclusion of bumper primers Seq ID No. 6 and Seq ID No. 7 in the reverse transcription reaction in addition to Seq ID No. 3 and Seq ID No. 5. This assay is used to detect mRNA in clinical specimens from patients receiving treatment for pulmonary tuberculosis and to determine the effects of antimicrobial agents on the expression of α-antigen mRNA in vitro.

EXAMPLE 4

Increased Sensitivity of the RT-SDA Assay

The reverse transcriptase-SDA system described above subsequently has been modified to increase sensitivity and robustness. Reverse transcription reactions were performed in 20 µl volumes as follows: Target mRNA was added to buffer containing (final concentrations) 30 mM K$_i$PO$_4$, 12% DMSO, 1250 nM Seq ID No. 3, 125 nM Seq ID No. 5, 12.5 nM Seq ID No. 6, 1.25 nM Seq ID No. 7, 0.8 mM dC$_S$TP, 0.2 mM dA-, dG- and dUTP, 2 mM magnesium acetate, 300 ng human placental DNA, 5 µg BSA, 1 U UDG and 1 U Prime RNase Inhibitor™ (5 Prime-3 Prime, Inc.). Reaction mixtures were incubated at 45° C. for 15 min to facilitate removal of contaminating amplicons by the UDG enzyme before addition of 4 U UDG inhibitor and 2.5 U AMV reverse transcriptase (Boehringer Mannheim). Reverse transcription was carried out for 15 min at 45° C. Tubes were then equilibrated at 52.5° C. for 3 min and SDA was initiated at the same temperature in a final volume of 50 µl through addition of K$_i$PO$_4$, DMSO, Seq ID No. 1 and Seq ID No. 4, dC$_S$TP, dUTP, dATP, dGTP, human placental DNA, magnesium acetate, BsoBI and Bst polymerase to the final concentrations indicated above for the modified DNA assay. Incubation was continued for 45 min before reactions were stopped by heating at 95° C. for 3 min. The products of amplification were detected using radiolabeled Seq ID No. 8 in primer extension assays or by chemiluminescence using Seq ID No. 9 and No. 10 (see Example 6, below). Coupled to this reverse transcriptase-SDA assay, both of these detection formats provide a reproducible analytical sensitivity of 10 in vitro transcripts of the *M. tuberculosis* α-antigen gene.

EXAMPLE 5

RT-SDA for α-antigen mRNA to Monitor Therapeutic Efficacy

Figure 3A:
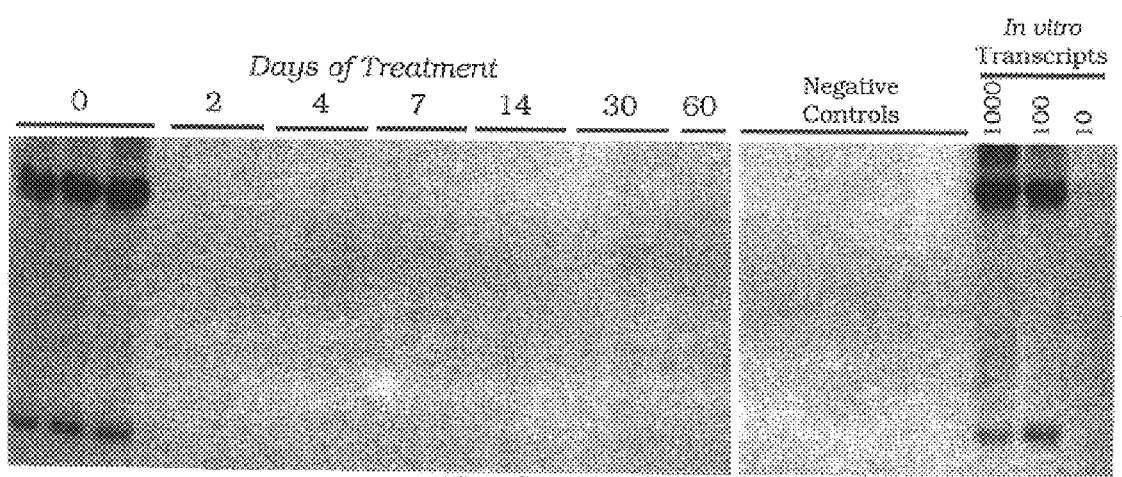
FIG. 3A shows the results of RT-SDA for *M. tuberculosis* α-antigen mRNA. Only specimens obtained prior to the start of treatment were positive. Control reactions without AMV reverse transcriptase were all negative, indicating the absence of contaminating DNA in the RNA samples (FIG. 3B).
Figure 3B:
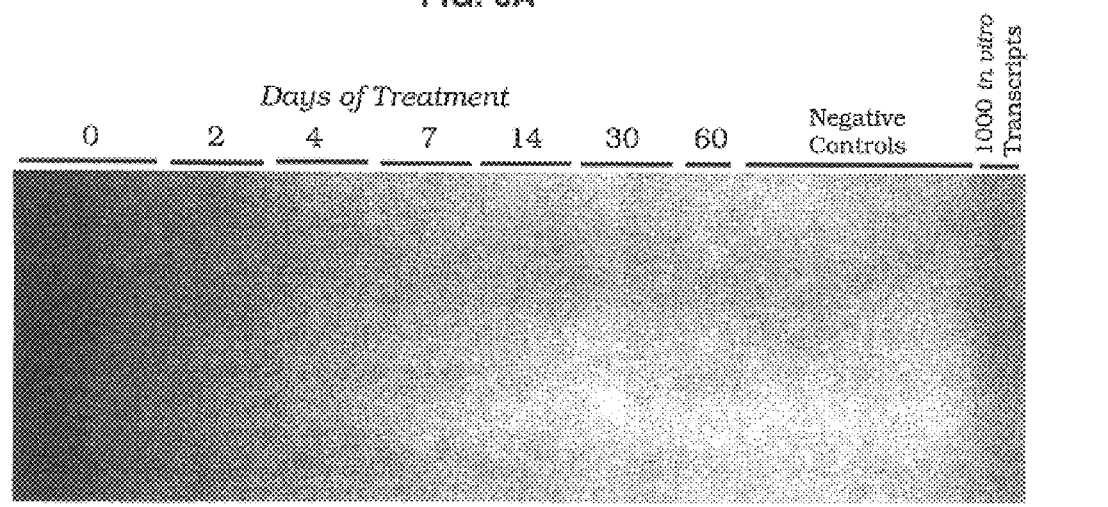
FIG. 3 shows the results of an RT-SDA experiment. RNA and DNA were isolated in separate fractions from sequential sputum specimens obtained from a patient who was treated for pulmonary tuberculosis.
FIG. 3C depicts the results of SDA of α-antigen DNA obtained from the same sputum specimens. The DNA assay remained positive for 14 days after the start of treatment and, in contrast with the RT-SDA results, these data did not reflect the observed drop in the number of viable organisms present per milliliter of sputum.

FIG. 3A shows the results of α-antigen RT-SDA performed on RNA isolated from sequential sputum specimens obtained from a patient with pulmonary tuberculosis. The patient was treated with a combination of four antimycobacterial drugs: isoniazid, rifampin, ethambutol and pyrazinamide. *M. tuberculosis* RNA and DNA were isolated in separate fractions using a modified guanidinium-phenol extraction procedure (DesJardin et al, 1996). RT-SDA was carried out as described in Example 4 on 1:500 dilutions of the RNA obtained from each sample. Positive RT-SDA results were only obtained from specimens collected before the start of treatment (Day 0). DNA contamination of the RNA samples was monitored by performing control reactions without AMV reverse transcriptase (FIG. 3B). No positive results were obtained from any of these controls indicating the absence of contaminating *M. tuberculosis* DNA.

Figure 3C:
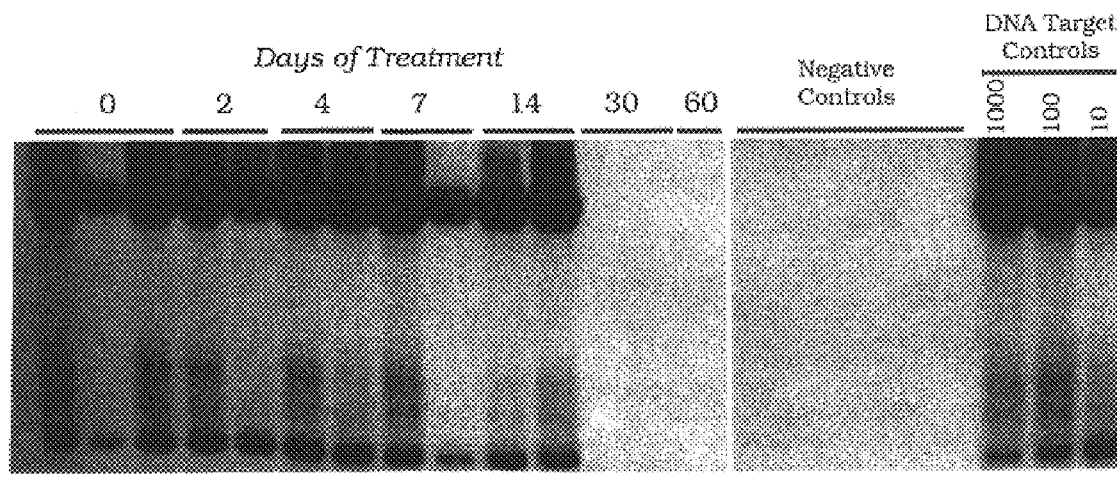

SDA for *M. tuberculosis* α-antigen was also performed on 1:500 dilutions of the DNA recovered from these sputum specimens, as described in Example 2. In contrast with the RT-SDA results for mRNA, α-antigen DNA was detected up 14 days after the start of treatment with no appreciable decrease in signal intensity before that time (FIG. 3C). Over the same time period the number of viable *M. tuberculosis* bacilli present per milliliter of sputum fell to approximately 0.03% of the initial value on Day 0. These data reflect the greater stability of DNA over RNA and the close correlation between *M. tuberculosis* α-antigen mRNA expression and bacterial viability. The levels of α-antigen mRNA present in the sputum of patients receiving effective chemotherapy for tuberculosis are expected to correlate closely with the observed drop in the number of viable organisms and be a useful marker of therapeutic efficacy.

EXAMPLE 6

Chemiluminescent Detection of SDA Products

Figure 4:
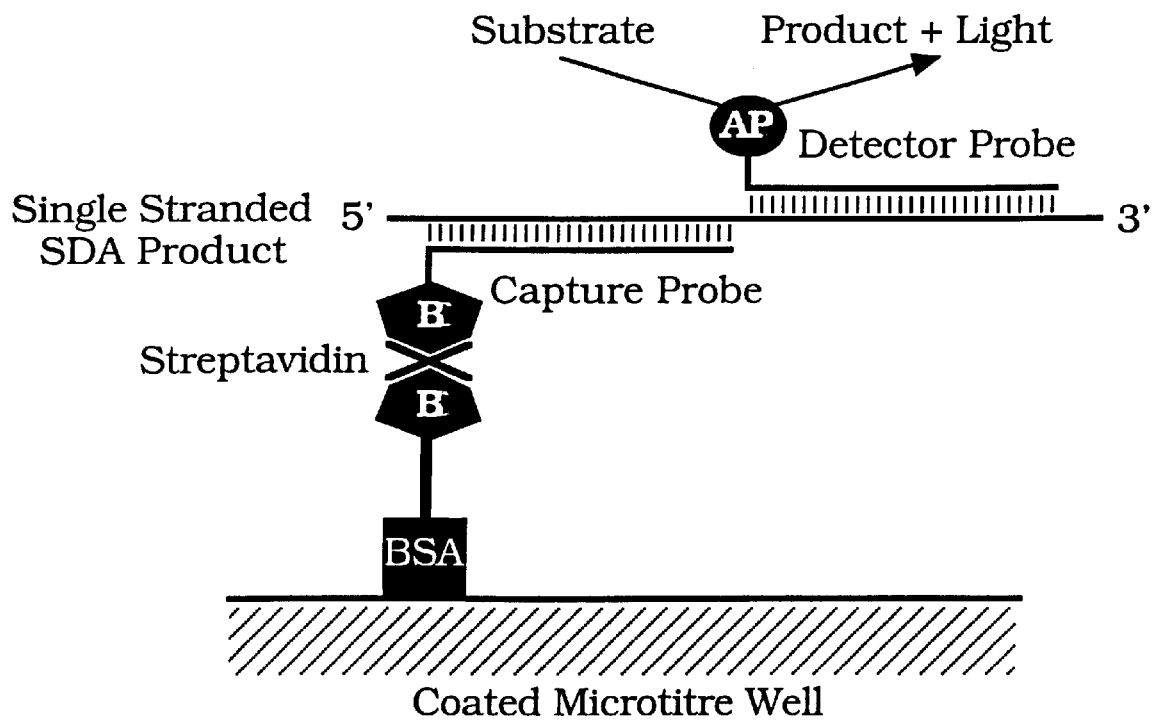
FIG. 4 is a schematic representation of chemiluminescent detection of SDA products.

A chemiluminescent assay for the detection of the products of amplification of the nt 415–571 region of the *M. tuberculosis* α-antigen gene has been developed. This assay is based on the procedure described by Spargo et al (1993) which relies upon the hybridization of amplified DNA to a biotinylated oligonucleotide which is in turn captured to the surface of a streptavidin-coated microtiter plate (FIG. 4). Captured target is detected by hybridization of an alkaline phosphatase-conjugated detector probe and addition of a chemiluminescent substrate after the wells are washed to remove unhybridized probes. Light emitted from the breakdown of substrate by the alkaline phosphatase enzyme is detected using a luminometer.

The optimized chemiluminescent assay employed Seq ID No. 9 and No. 10 as the capture and detector probes, respectively.

Seq ID No. 9 possesses a 3' biotin moiety while Seq ID No. 10 is conjugated at its 3' end to alkaline phosphatase. 5'-biotinylation of Seq ID No. 9 yielded consistently lower luminescent values than when the biotin group was attached at the 3' end, presumably because of steric hindrance with the 3'-phosphatase of Seq ID No. 10.

In brief, amplified products were denatured by boiling, cooled to room temperature, and 10 µl of a 1:10 dilution in 50 mM K$_i$PO$_4$, pH 7.6 was mixed with 0.75 pmol Seq ID No. 9 and 0.125 pmol Seq ID No. 10 in 90 µl buffer containing (final concentrations) 50 mM Tris, pH 7.0; 900 mM NaCl; 50 mM ZnCl$_2$; 1 µg salmon sperm DNA; 0.01% bovine serum albumin and 0.07% NaN$_3$. Microtiter plates were incubated at 37° C. for 45 min before each well was washed three times with 300 µl stringency wash (250 mM NaCl; 10 mM Tris, pH 7.5; 0.1% BSA; 0.01% igepal and 0.1% NaN$_3$). One hundred microliters of the chemiluminescent substrate Lumiphos 530 was than added and plates were incubated a further 40 min at 37° C. before reading in a Labsystems Luminoskan Luminometer.

Using this chemiluminescent detection system coupled to the SDA assays described above, the ability to detect as few as 10 copies of *M. tuberculosis* α-antigen DNA or mRNA was demonstrated.

EXAMPLE 7

Fluorescence Polarization-Based Detection of SDA Products

As an alternative to detection of the products of amplification by primer extension analysis or chemiluminescent assay, the above α-antigen DNA and mRNA assays have been adapted to a fluorescence polarization (FP)-based detection format. In this system, FP was used to detect the conversion of a fluorescently-labeled detector probe from a single-stranded form to a double-stranded form during the amplification process (Walker et al, 1996). Fluorescein-labeled Seq ID No. 8 was included in the SDA buffer at a final concentration of 5 nM and the reactions were stopped by freezing in a dry ice-ethanol bath, otherwise all reaction conditions are as described for the modified DNA amplification system above. After the reaction was complete, 45 µl of amplified sample were removed, diluted to 1 ml in buffer containing 40 mM K$_i$PO$_4$; 5 mM MgCl$_2$; 2.5% glycerol; 3% DMSO and 0.02 mg/ml BSA and FP values were determined using an FPM-1 Fluorescence Polarization Analyzer (Jolley Consulting & Research, Inc.). An analytical sensitivity for the FP-based assays of 100 copies of *M. tuberculosis* complex α-antigen DNA or mRNA was demonstrated in the present invention. FP offers significant time saving advantages over isotopic or chemiluminescent detection with the potential of real-time detection in a sealed vessel without the need for post amplification manipulation (Devlin et al, 1993; Walker et al, 1996).

EXAMPLE 8

RT-SDA of Target mRNA Captured on Magnetic Beads

Figure 5A:
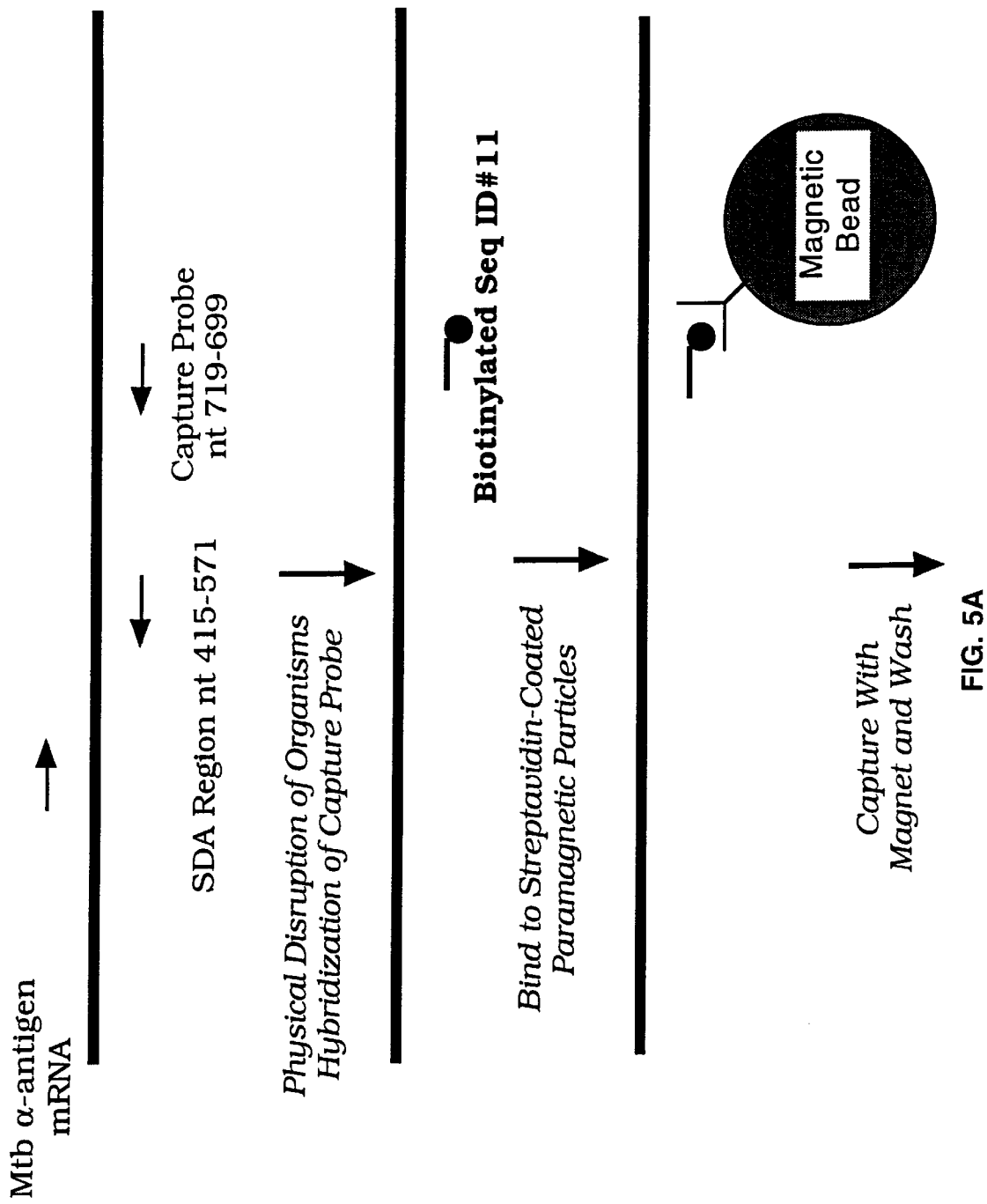
FIG. 5 is a schematic representation of the procedure for specific recovery of *M. tuberculosis* α-antigen mRNA from clinical samples, using a biotinylated capture probe which hybridizes to the target sequence. Captured target is recovered using strepavidin-coated paramagnetic particles and the particles are then washed to remove contaminating DNA and protein. RT-SDA may then be performed by adding a suspension of the beads directly to a reverse transcription reaction.
Figure 5B:
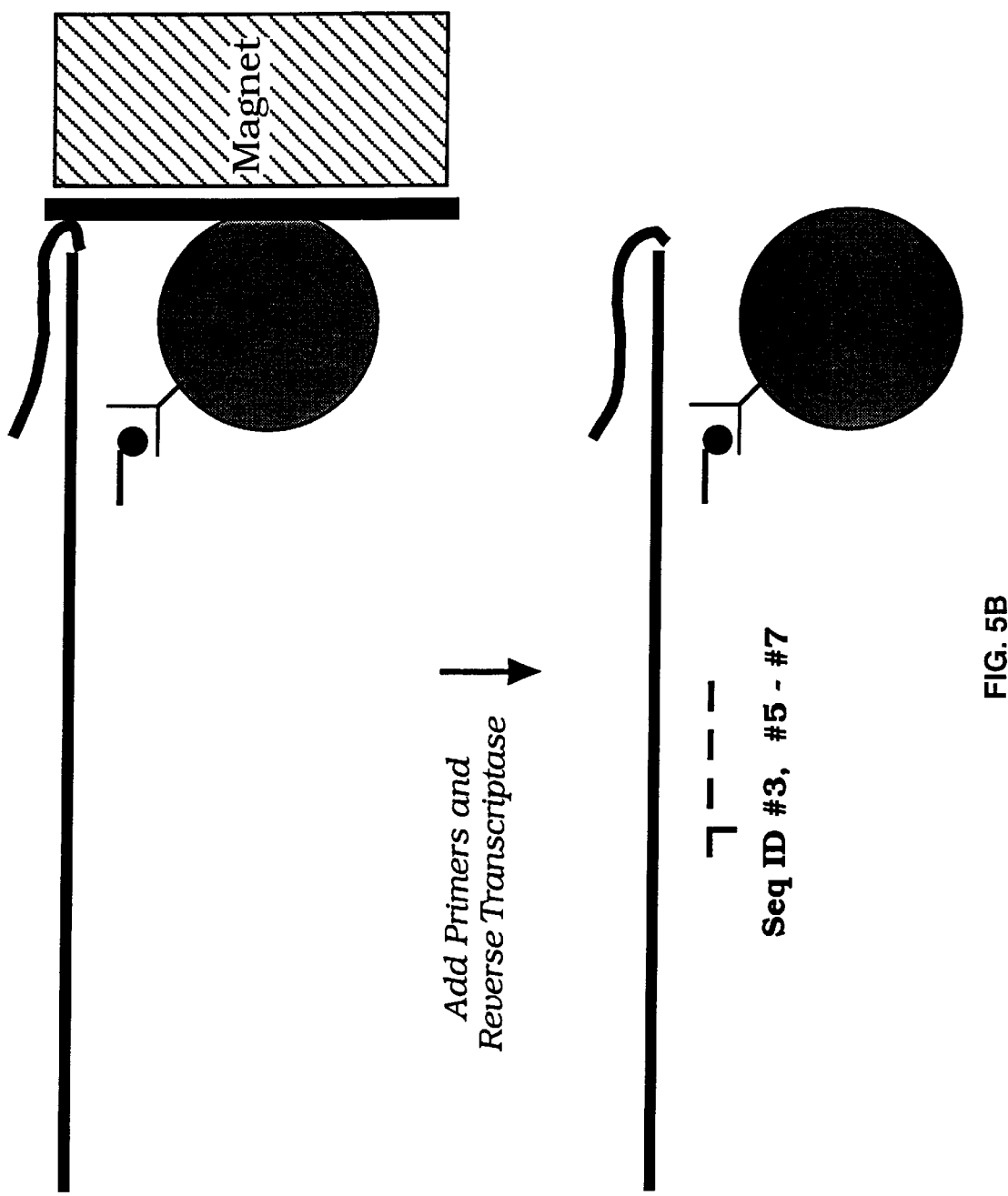

Isolation of intact bacterial RNA from clinical specimens presents particular problems owing to the presence of endogenous highly stable RNases. A method which facilitates the extraction of RNA from mycobacteria in sputum has been developed which combines physical disruption of cells in guanidinium isothiocyanate and extraction with organic solvent (DesJardin et al, 1996). However, this protocol is very labor intensive and requires the use of toxic reagents which preclude its application in a clinical laboratory. Therefore a procedure was developed for the specific recovery of *M. tuberculosis* α-antigen mRNA from clinical samples using a biotinylated capture probe (Seq ID No. 11) which hybridizes to the target sequence. Captured target was recovered using streptavidin-coated paramagnetic particles which were washed to remove contaminating DNA and protein (FIG. 5). Reverse transcriptase-SDA was then performed by addition of a suspension of the beads directly to a reverse transcription reaction. This system was currently under development but in the clean, cell-free system described below, specific (i.e. Seq ID No. 11-dependent) recovery and subsequent reverse transcriptase-mediated amplification with an input of as few as 1000 target transcripts has been achieved against a background of 10 ng/µl contaminating yeast RNA.

In brief, 20 pmol 5'-biotinylated Seq ID No. 11 was hybridized to target mRNA for 30 min at room temperature in hybridization buffer containing 100 mM Tris, pH 8; 1M LiCl; 10 mM EDTA; 0.1% lithium dodecyl sulfate; 5 mM dithiothreitol; 10 ng/µl yeast RNA (Ambion). Two hundred micrograms of streptavidin coated paramagnetic beads (Promega) which had been washed three times in hybridization buffer were then added and incubation continued for another 30 min. Tubes were then placed in a magnetic stand to capture the beads. Hybridization buffer was decanted and the beads were washed twice in 10 mM Tris, pH8; 150 mM LiCl; 1 mM EDTA and twice more in 30 mM K$_i$PO$_4$, pH 7.6. After removal of the final wash, the beads were resuspended in 10 µl water containing 10 ng/µl yeast RNA and 5 µl of this suspension was used in reverse transcriptase-SDA.

EXAMPLE 9

Multiplex RT-SDA Assays

Figure 6A:
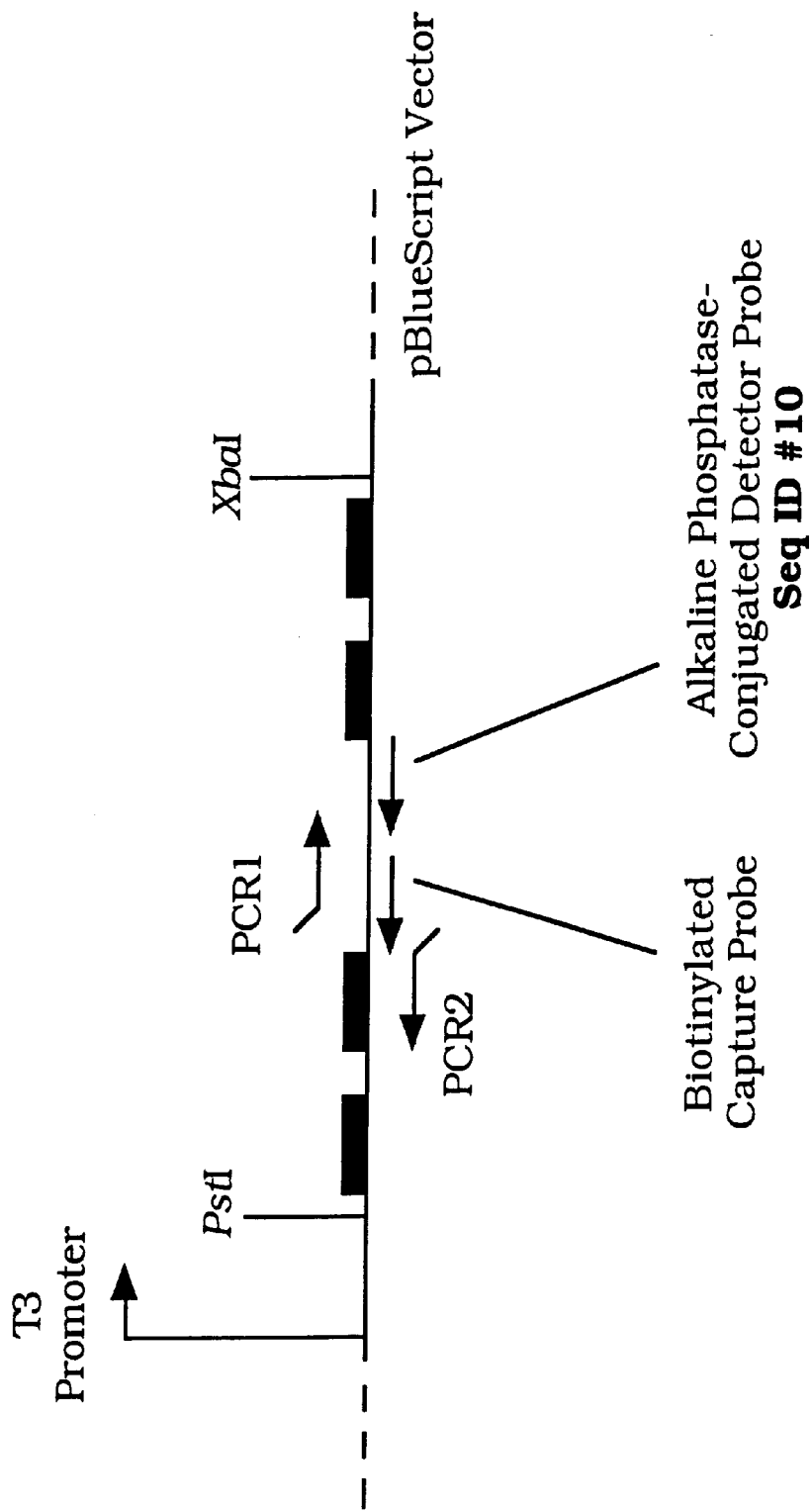
FIG. 6A depicts the strategy for cloning of internal control sequences for RT-SDA of *M. tuberculosis* α-antigen. Solid bars represent the binding regions of the SDA and bumper primers. PCR1, 5'-gCA CgC CCA CCg gCA gCg C-3' (SEQ. ID No. 18); PCR2, 5'-TCA CCC TgT Tgg Cgg ACA ACC A-3' (SEQ. ID No. 19). Bases shown in bold face type represent those that differ from the native *M. tuberculosis* complex target (see FIG. 6B). After initial cloning in pBlueScript, the internal control sequence was subcloned into the PstI-XbaI sites of the vector pSP64 Poly(A) (Promega) to facilitate purification of in vitro transcripts by binding to oligo(dT) cellulose.
Figure 7A:
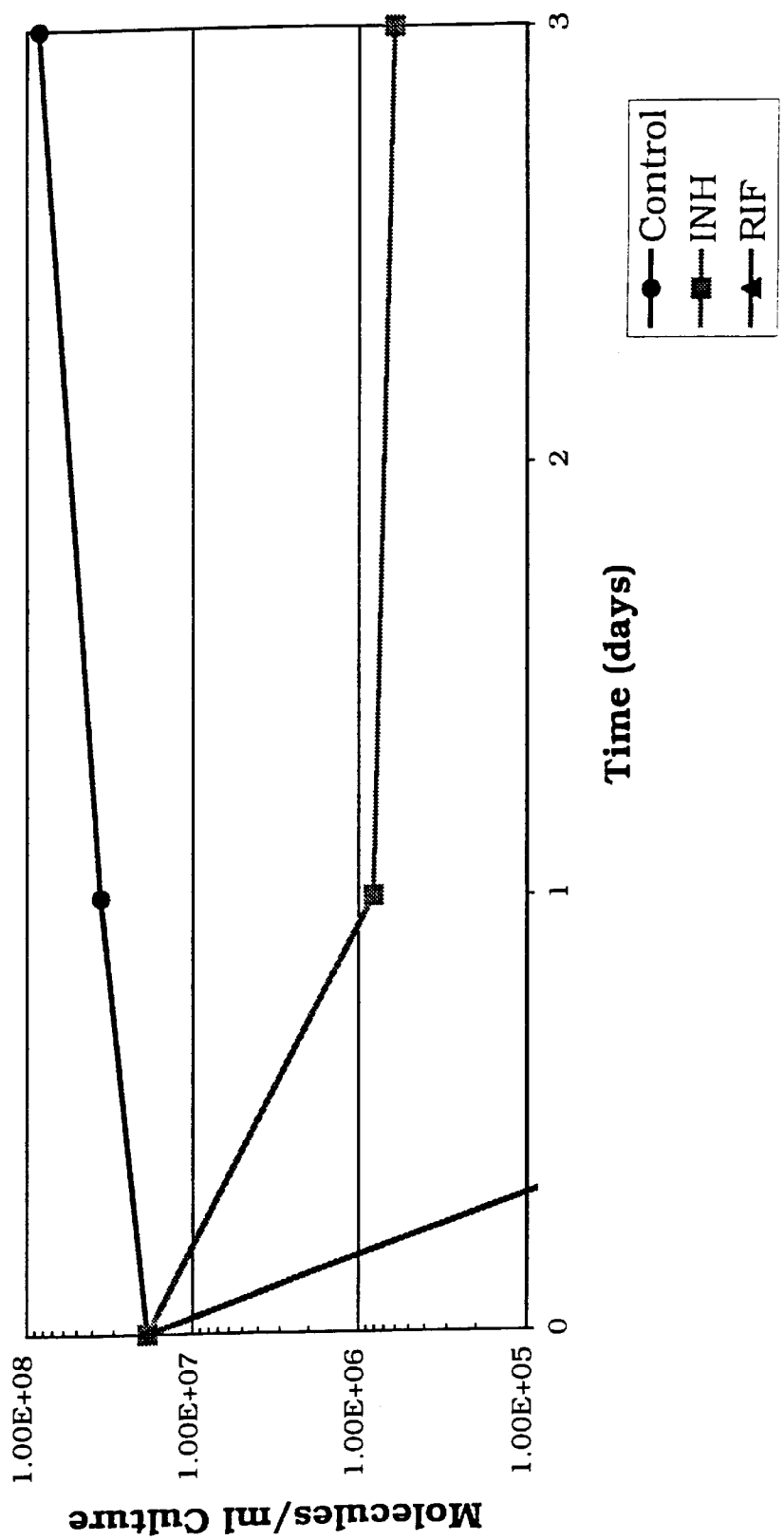
FIGS. 7A, B show the effects of anti-mycobacterial agents on expression of *M. tuberculosis* α-antigen mRNA. Quantitative RT-PCR was used to discriminate drug-resistant and drug-susceptible organisms. Isoniazid (INH) or rifampin (RIF) was added to log-phase cultures of *M. tuberculosis* and mycobacterial RNA was isolated from samples taken at predetermined timepoints. Quantitative RT-PCR was performed for the α-antigen mRNA using a 5' fluorogenic nuclease assay and an Applied BioSystems Prism 7700 Sequence Detection System with primers selected from Table 1. By this means susceptible and resistant organisms could easily be discriminated. Changes in α-antigen mRNA expression were detected within 24 hours of exposure to either INH or RIF.
Figure 7B:
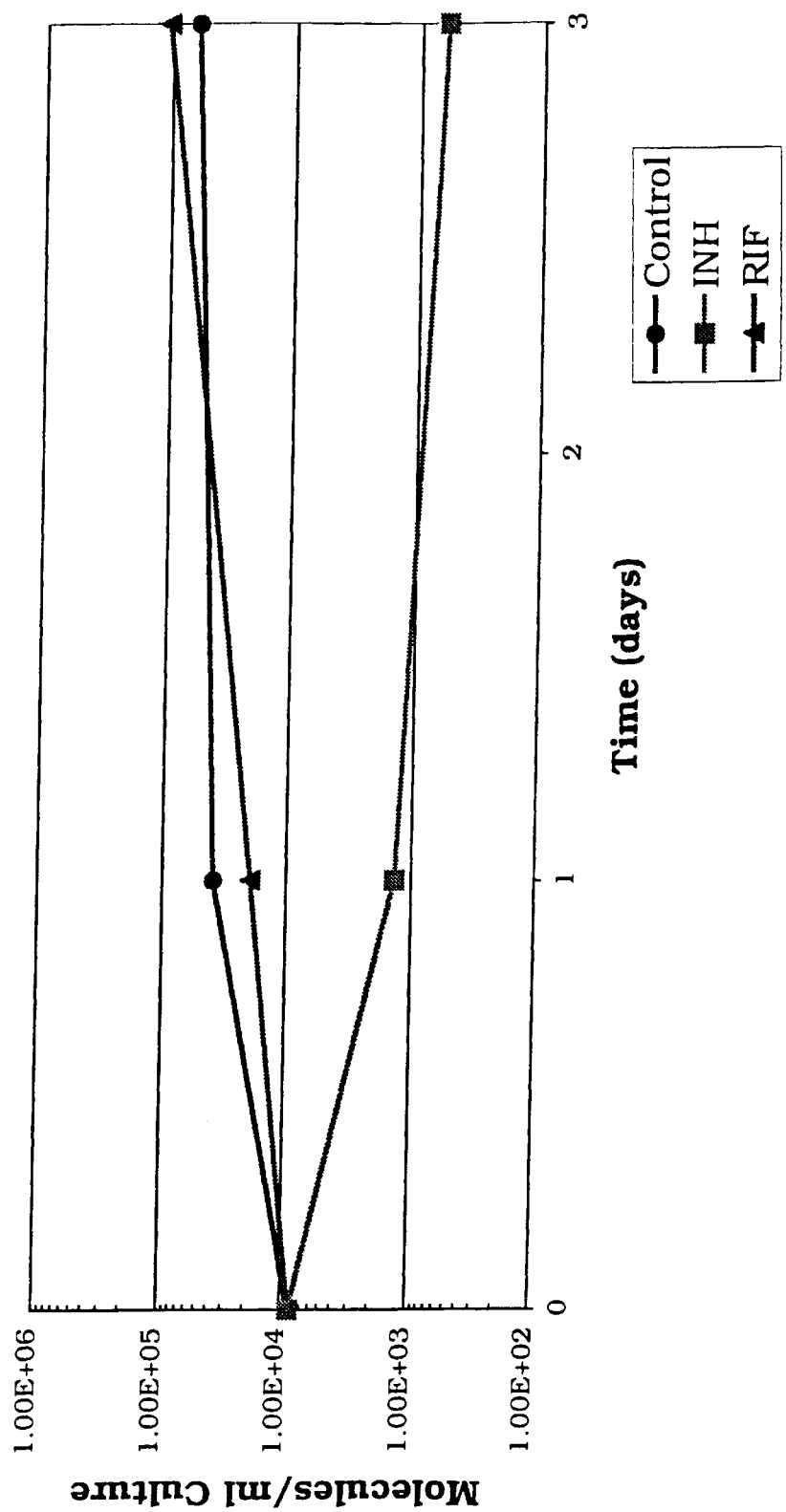
Figure 8:
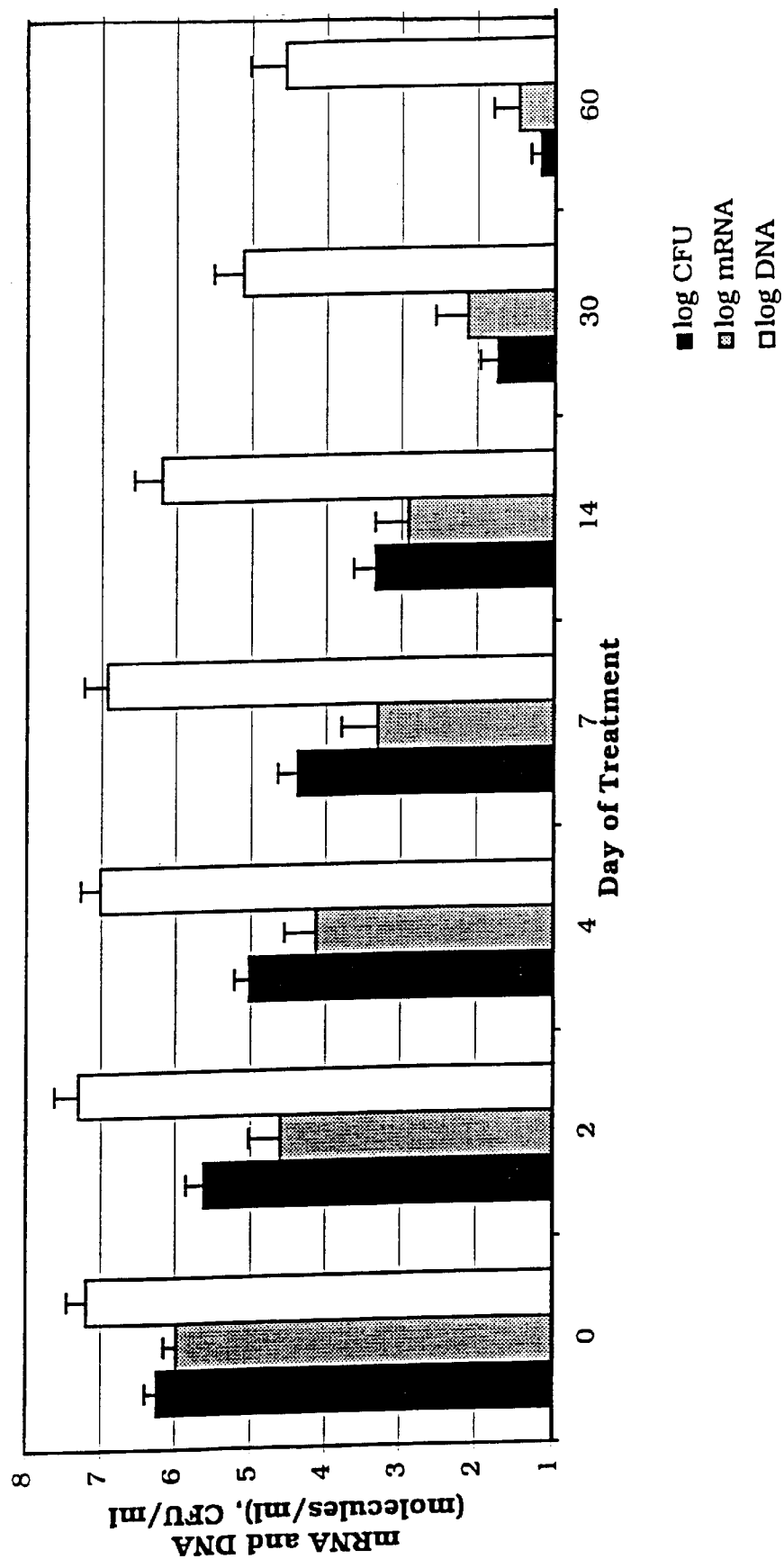
FIG. 8 shows a comparison between viable counts and levels of *M. tuberculosis* DNA and mRNA in sputum from 20 patients who were treated for pulmonary tuberculosis. DNA levels were assessed by quantitative PCR for the *M. tuberculosis* complex-specific insertion element IS6110. Quantitative RT-PCR for *M. tuberculosis* α-antigen mRNA was performed using primers selected from Table 1. The rate at which α-antigen mRNA levels declined was similar to that seen for the numbers of viable bacilli. In contrast, IS6110 DNA persisted at much higher levels throughout the first 60 days of treatment.

In order to control for the efficiency of reverse transcription and amplification, an internal control molecule which is amplified in the same reaction and using the same primers as native *M. tuberculosis* α-antigen target mRNA has been developed. This control molecule was constructed by cloning the 414–523 nt region of the *M. tuberculosis* H37R$_v$ α-antigen gene into the PstI and XbaI sites of pBlueScript KS+. Outward-facing PCR primers were designed which incorporated a six-base mutation in the region internal to Seq ID No. 1 and Seq ID No. 3 and spanning the Seq ID No. 9 sequence FIG. 6). Inverse PCR was performed with Pfu DNA polymerase (Stratagene) using these primers and the ends of the product were ligated to generate a circular plasmid molecule which was electroporated into *E. coli*. In order to facilitate purification of in vitro transcripts by binding to oligo-(dT) cellulose, the cloned fragment was excised from pBlueScript and subcloned into the plasmid vector pSP64 Poly (A) (Promega) which possesses a polyadenylation sequence downstream of the multiple cloning site. In vitro transcripts with a 30 base poly-(A) tail were generated and purified using an Ambion MEGAscript™ SP6 Kit according to the manufacturer's instructions.

The resulting control transcripts amplify with similar efficiency to native *M. tuberculosis* target but the two can be distinguished when co-amplified in the same reverse transcriptase-SDA reaction using chemiluminescence or fluorescence polarization-based detection formats. For chemiluminescent detection of internal control, a 3'-biotinylated capture probe with the sequence 5'-gCg Tgc TCA CCC T (SEQ ID NO. 20) was used in place of Seq ID No. 9, while the same alkaline phosphatase-conjugated detector sequence (Seq ID No. 10) is employed for both the M. tuberculosis and control targets.

For fluorescence polarization-based detection of the internal control, a 5'-fluorescein-labeled detector probe with the sequence 5'-CgC TgC Cgg Tgg gCg TgC TgC TC (SEQ. ID No. 21) is added to the reaction mixture as previously described. Limitations of available instrumentation currently preclude co-detection of M. tuberculosis and internal control target in the same tube, however a "duplex" format whereby target mRNA is added to each of two reverse transcriptase-SDA reactions containing control transcripts and detector probe for either M. tuberculosis or the internal control has been developed. In the presence of 5000 control mRNA molecules, the analytical sensitivity of this system is currently in the order of 100 M. tuberculosis α-antigen targets.

EXAMPLE 10

Identification of Primers for RT-PCR

RT-PCR primers were based on published sequences of the α-antigen genes from M. tuberculosis strain Erdman, M. bovis strain 1173P2 (De Wit et al, 1994) and M. bovis BCG strain Tokyo (Matsuo et al, 1988). Computer-assisted alignment was carried out with the α-antigen gene sequences of M. avium* (Ohara et al, 1993), *M. intracellulare* (Kitaura et al, 1993), *M. scrofulaceum* (Takano et al, 1994), *M. kansasii* (Matsuo et al, 1990) and *M. leprae* (De Lima et al, 1991). Primer sequences are listed in Table 1 and their positions within the *M. tuberculosis* α-antigen gene are shown diagrammatically in FIG. 1.

SEQ ID No. 14 is for use as a detector probe with the Applied BioSystems Prism 7700 Sequence detection System. This primer is coupled at its 5' end to 5-carboxyfluorescein while at its 3' end an additional T residue is added which is not present in the native *M. tuberculosis* sequence. This 3' T residue is in turn coupled to N,N,N',N'-tetramethyl-6-carboxyrhodamine.

SEQ ID No. 12 is a sense primer from nt 588–605 while SEQ ID No. 13 is an antisense primer spanning nt 718–699. SEQ ID No. 13 is used in reverse transcription of the α-antigen mRNA to cDNA. Both SEQ ID No. 12 and SEQ ID No. 13 are used for PCR amplification of *M. tuberculosis* α-antigen DNA. SEQ ID No. 14 is a sense primer from nt 667–689 and is the detector primer for use in 5' fluorogenic exonuclease assays.

The specificity of the SEQ ID Nos. 12–14 was tested in 5' fluorogenic nuclease PCR assays for cross-reaction with DNA from 9 other species of mycobacteria comprising 10 strains of *M. avium—M. intracellulare,* seven of *M. fortuitum,* five of *M. xenopi,* four of *M. malmoense,* three of *M. kansasii,* three of *M. chelonei,* and one each of *M. scrofulaceum, M. gordonae* and *M. celatum.* No cross-reaction was observed after 40 cycles of PCR with any of this panel of strains nor with any of the following phylogenetically related non-mycobacterial species: *Streptomyces albus, Rhoddococcus rhodochrous, Nocardia braziliensis, Corynebacterium diphtheriae* or *Actinomyces israeli.*

EXAMPLE 11

Rapid Determination of Antimycobacterial Drug Susceptibility

Quantitative RT-PCR for *M. tuberculosis* α-antigen mRNA was used as a means to discriminate drug-resistant and drug-susceptible organisms. Isoniazid (INH) or rifampin (RIF) was added to log-phase cultures of *M. tuberculosis* which were then incubated a further 3 days. Samples were removed on days 0, 1, and 3 for nucleic acid extraction and plating on solid medium. Mycobacterial RNA and DNA were isolated in separate fractions using a modified guanidinium-phenol procedure (DesJardin et al, 1996). Reverse transcription of isolated mRNA was carried out using SEQ ID No. 13 and AMV reverse transcriptase. The resulting cDNA was amplified by PCR in a 5' fluorogenic nuclease assay using an Applied BioSystems Prism 7700 Sequence Detection System. SEQ ID No. 12 and SEQ ID No. 13 were employed as PCR primers while fluorescently labeled SEQ ID No. 14 was used as the detector probe. Results were compared with those of a quantitative 5' fluorogenic exonuclease-based assay for the DNA of the *M. tuberculosis* complex-specific insertion element IS6110, an isotopic RT-PCR assay for 16S ribosomal RNA and viable counts on solid media.

Loss of viability as determined by colony counts was not reflected by changes in the levels of detectable DNA or ribosomal RNA (data not shown). In contrast, susceptible and resistant organisms could easily be discriminated by quantitative RT-PCR of α-antigen mRNA (FIG. 7). Changes in α-antigen mRNA were detected within 24 hours of exposure to either INH or RIF although the decline in detectable mRNA was more rapid for RIF-treated cultures. Analysis of mRNA offers the potential for rapid determination of drug susceptibility.

EXAMPLE 12

RT-PCR for α-antigen mRNA to Monitor Therapeutic Efficacy

Levels of *M. tuberculosis* α-antigen mRNA and IS6110 DNA in sputum were examined as potential indicators of response to chemotherapy in patients with tuberculosis. Sputum specimens were collected serially from 20 patients with smear-positive pulmonary tuberculosis on days 0, 2, 4, 7, 14, 30 and 60 after the start of a standard four drug treatment regimen comprising isoniazid, rifampin, ethambutol, and pyrazinamide. Mycobacterial RNA and DNA were isolated in separate fractions using a modified guanidine-phenol extraction procedure (DesJardin et al, 1996). Quantitative RT-PCR was performed using SEQ ID Nos. 12–14 in a 5' fluorogenic exonuclease assay with an Applied BioSystems Prism 7700 Sequence Detection System. A fluorogenic exonuclease assay was also employed for quantification of *M. tuberculosis* complex-specific IS6110 DNA. Nucleic acid levels were compared with the number of viable bacilli present per milliliter of sputum as determined by colony counts on solid medium.

Levels of α-antigen mRNA declined rapidly in the first 2 weeks of therapy as did viable colony counts (FIG. 8). The mean number of viable organisms/ml of sputum fell to 1.3% of the initial value by day 7 of treatment and to 0.1% by day 14. Similarly, mean α-antigen mRNA levels were 0.2% of their pretreatment value by day 7 and 0.08% by day 14. In contrast, however, the level of IS6110 DNA fell to only 50% of its initial value by day 7 and to 10% by day 14. In 18/20 (90%) patients studied neither viable bacilli nor α-antigen mRNA were detectable by day 60. The rapid reduction in α-antigen mRNA appears to reflect chemotherapeutic efficacy and clearance of viable organisms from sputum.

EXAMPLE 13

Comparison of End-point Dilution and Fluorogenic RT-PCR

Results similar to those obtained with the above quantitative 5' fluorogenic nuclease assay were also obtained by endpoint dilution analysis. Serial 5-fold dilutions of the RNA isolated from sequential sputum samples were prepared and amplified by RT-PCR using radiolabeled SEQ ID No. 12 and SEQ ID No 13. The products of amplification were analyzed by autoradiography and the last dilution at which a positive result was obtained was defined as the end-point titer. Based upon the analytical sensitivity of the PCR amplification and the efficiency of reverse transcription, the calculated number of mRNA molecules present in the original sputum samples was the same as determined by both the fluorogenic and isotopic assays.

References

Belasco J G, Nilsson G, von Gabain A, Cohen S N. The stability of *E. coli* gene transcripts is dependent on determinants localized to specific mRNA segments. *Cell* 1986; 46: 245–251.

Collett M S, Leis J P, Smith M S and Faras A J. Unwinding-like activity associated with avian retrovirus RNA-directed DNA polymerase. *J Virol* 1978; 26: 498–509.

Compton J. Nucleic acid sequence-based amplification. *Nature (London)* 1991; 350:91–92.

Desjardin L E, Perkins M D, Teixeira L, Cave M D and Eisenach K D. Alkaline decontamination of sputum specimens adversely affects stability of mycobacterial mRNA. *J Clin Microbiol* 1996; 34: 2435–2439.

Devlin R, Studholme R M, Dandliker W B, Fahy E, Blumeyer K and Ghosh S S. Homogeneous detection of nucleic acids by transient-state polarized fluorescence. *Clin Chem* 1993; 39: 1939–1943.

Eisenach K D, Sifford M D, Cave M D, Bates J H and Crawford J T. Detection of *Mycobacterium tuberculosis* in sputum samples using a polymerase chain reaction. *Am Rev Respir Dis* 1991; 144: 1160–1163.

von Gabain A, Belasco J G, Schottel J L, Chang A C Y and Cohen S N. Decay of mRNA in *Escherichia coli:* investigation of the fate of specific segments of transcripts. *Proc Natl Acad Sci USA* 1983; 80: 653–657.

Gingeras T R, Whitfield K M, and Kwoh D Y. Unique features of the self-sustained sequence replication (3SR) reaction in the in vitro amplification of nucleic acids. *Ann Biol Clin* 1990; 48:498–501.

Harth G, Lee B-Y, Wang J, Clemens D L and Horwitz M A. Novel insights into the genetics, biochemistry, and immunocytochemistry of the 30-kilodalton major extracellular protein of *Mycobacterium tuberculosis. Infect Immun* 1996; 64: 3038–3047.

Hellyer T J, Fletcher T W, Bates J H, Stead W W, Templeton G L, Cave M D and Eisenach K D. Strand displacement amplification and the polymerase chain reaction for monitoring response to treatment in patients with pulmonary tuberculosis. *J Infect Dis* 1996; 173: 934–941.

Holland P M, Abramson R D, Watson R and Gelfand D H. Detection of specific polymerase chain reaction product by utilizing the 5' to 3' exonuclease activity of *Thermus aquaticus* DNA polymerase. *Proc Natl Acad Sci USA* 1991; 88:7276–7280.

Iovannisci D M and Winn-Deen E S. Ligation amplification and fluorescence detection of *Mycobacterium tuberculosis* DNA. *Mol Cell Probes* 1993; 7: 35–43.

Jonas V, Alden M J, Curry J I, Kamisango K, Knott C A, Lankford R, Wolfe J M and Moore D F. Detection and identification of *Mycobacterium tuberculosis* directly from sputum sediments by amplification of rRNA. *J Clin Microbiol* 1993; 31: 2410–2416.

Kramer F R, Lizardi P M and Tyagi S. Qβ amplification assays. *Clin Chem* 1992; 38:456–457.

Kitaura H, Ohara N, Matsuo T, Tasaka H, Kobayashi K and Yamada T. Cloning, sequencing and expression of the gene for α-antigen from *Mycobacterium intracellulare* and use of PCR for the rapid identification of *Mycobacterium intracellulare. Biochem Biophys Res Comm* 1993; 196: 1466–1473.

Lee B-Y and Horwitz M A. Identification of macrophage and stress-induced proteins of *Mycobacterium tuberculosis. J Clin Invest* 1995; 96: 245–249.

Lima L de M, Content J, van Heuverswyn H and Degrave W. Nucleotide sequence of the gene encoding for the 85-B antigen of *Mycobacterium leprae. Nucleic Acids Res* 1991; 19: 5789.

Livak K J, Flood S J A, Marmaro J, Giusti W, and Deetz K. Oligonucleotides with fluorescent dyes at opposite ends provide a quenched probe system useful for detecting PCR product and nucleic acid hybridization. *PCR Methods and Applications* 1995; 4:357–362.

Matsuo K, Yamaguchi R, Yamazaki A, Tasaka H, Terasaka K and Yamada T. Cloning and expression of the gene for the cross-reactive a antigen of *Mycobacterium kansasii. Infect Immun* 1990; 58: 550–556.

Matsuo K, Yamaguchi R, Yamazaki A, Tasaka H and Yamada T. Cloning and expression of the *Mycobacterium bovis* BCG gene for extracellular α-antigen. *J Bacteriol* 1988; 170: 3847–3854.

Moore D F, Curry J I, Knott C A and Jonas V. Amplification of rRNA for assessment of treatment response of pulmonary tuberculosis patients during antimicrobial therapy. *J Clin Microbiol* 1996; 34: 1745–1749.

Ohara N, Matsuo K, Yamaguchi R, Yamazaki A, Tasaka H and Yamada T. Cloning and sequencing of the gene for α-antigen from *Mycobacterium avium* and mapping of B-cell epitopes. *Infect Immun* 1993; 61: 1173–1179.

Raviglione M C, Snider D E, Kochi A. Global epidemiology of tuberculosis: morbidity and mortality of a worldwide epidemic. *J A M A* 1995; 273: 220–226.

Saiki R K, Scharf S, Faloona F, Mullis K B, Horn G T, Erlich H A and Arnheim N. Enzymatic amplification of beta-globin genomic sequences and restriction site analysis for diagnosis of sickle cell anemia. *Science* 1985; 230:1350–1354.

Shah J S, Liu J, Buxton D, Hendricks A, Robinson L, Radcliffe G, King W, Lane D, Olive D, Olive D M and Klinger J D. Q-Beta replicase-amplified assay for detection of *Mycobacterium tuberculosis* directly from clinical specimens. *J Clin Microbiol* 1995; 33: 1435–1441.

Soini H, Bottger E C and Viljanen M K. Identification of mycobacteria by PCR-based sequence determination of the 32-kilodalton protein gene. *J Clin Microbiol* 1994; 32: 2944–2947.

Spargo C A, Haaland P D, Jurgensen S R, Shank D D and Walker G T. Chemiluminescent detection of strand-displacement amplified DNA from species comprising the *Mycobacterium tuberculosis* complex. *Mol Cellular Probes* 1993; 7:395–404.

Takano M, Ohara N, Mizuno A and Yamada T. Cloning, sequencing and expression in Escherichia coli of the gene for α-antigen from *Mycobacterium scrofulaceum. Scand J Immunol* 1994; 40: 165–170.

van der Vliet G M E, Schukkink R A F, van Gemen B, Schepers P and Klatser P R. Nucleic acid sequence-based amplification (NASBA) for the identification of mycobacteria. *J Gen Microbiol* 1993; 139: 2423–2429.

Walker G T, Fraiser M S, Schram J L, Little M C, Nadeau J G and Malinowski D P. Strand displacement amplification—an isothermal, in vitro DNA amplification technique. *Nucleic Acids Res* 1992; 20: 1691–1696.

Walker G T, Nadeau J G, Linn C P, Devlin R F and Dandliker W B. Strand displacement amplification (SDA) and transient-state fluorescence polarization detection of *Mycobacterium tuberculosis* DNA. Clin Chem 1996; 42:9–13.

Wolcott M J. Advances in nucleic acid-based detection methods. *Clin Microbiol Rev* 1992; 5:370–386.

Wiker H G and Harboe M. The antigen 85 complex: a major secretion product of *Mycobacterium tuberculosis*. *Microbiol Rev* 1992; 56: 648–661.

De Wit L, Palou M and Content J. Nucleotide sequence of the 85B-protein gene of Mycobacterium bovis BCG and *Mycobacterium tuberculosis*. *DNA Seq* 1994; 4: 267–270.

Wu D Y and Wallace R B. The ligation amplification reaction (LAR)—amplification of specific DNA sequences using sequential rounds of template-dependent ligation. *Genomics* 1989; 4:560–569.

Ying C and Desjardin L E D. Unpublished. 1995.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method for detecting viable organisms of *M. tuberculosis* complex in a clinical sample or in vitro culture, comprising the steps of:
   isolating mRNA from said sample or culture;
   adding said isolated mRNA to a buffer containing a primer having a sequence complementary to an *M. tuberculosis* α-antigen mRNA, nucleotides and reverse transcriptase to form a first mixture;
   incubating said first mixture to permit synthesis of cDNA by said reverse transcriptase using said isolated mRNA as template;
   adding an aliquot of said cDNA to a buffer containing one or more additional primers, nucleotides and a DNA polymerase to form a second mixture;
   incubating said second mixture through successive cycles of heating and cooling to facilitate synthesis of specific PCR products by said DNA polymerase;
   detecting said specific PCR products using a specific detector primer having the sequence shown in SEQ ID No. 14, wherein a presence of said PCR products indicates a presence of viable organisms of *M. tuberculosis* complex in said sample or culture and wherein an absence of said PCR products indicates an absence of viable organisms of *M. tuberculosis* complex in said sample or culture.

2. A method for detecting *Mycobacterium tuberculosis* DNA in clinical samples or in vitro cultures comprising the steps of:
   isolating DNA from said samples or cultures;
   adding said isolated DNA to a buffer containing two or more primers having the sequences shown in SEQ ID Nos. 12 & 13, SEQ ID Nos. 12 & 14, SEQ ID Nos. 13 & 14, or SEQ ID Nos. 12–14, nucleotides and a DNA polymerase to form a reaction mixture;
   incubating said reaction mixture through successive cycles of heating and cooling to facilitate synthesis of specific PCR products by said DNA polymerase;
   detecting said PCR products using a specific detector primer having the sequence shown in SEQ ID No. 14 wherein a presence of said specific PCR products indicates a presence of *M. tuberculosis* complex DNA in said sample or culture and wherein an absence of said specific PCR products indicates an absence of *M. tuberculosis* complex DNA from said sample or culture.

3. The method of claim 2, wherein said primers having the sequences shown in SEQ ID No. 12 and SEQ ID No. 13.

4. The method of claim 2, wherein said primers having the sequences shown in SEQ ID No. 12, SEQ ID No. 13 and SEQ ID No. 14.

5. A method for detecting viable organisms of *M. tuberculosis* complex in a clinical sample or in vitro culture, comprising the steps of:
   isolating mRNA from said sample or culture;
   adding said isolated mRNA to a buffer containing a first primer having a sequence selected from the group consisting of SEQ ID Nos. 12–14, nucleotides and reverse transcriptase to form a first mixture;
   incubating said first mixture to permit synthesis of cDNA by said reverse transcriptase using said mRNA as template;
   adding an aliquot of said cDNA to a buffer containing one or more additional primers, nucleotides and a DNA polymerase to form a second mixture;
   incubating said second mixture through successive cycles of heating and cooling to facilitate synthesis of specific PCR products by said DNA polymerase;
   detecting said specific PCR products using a specific detector primer having the sequence shown in SEQ ID No. 14, wherein a presence of said PCR products indicates a presence of viable organisms of *M. tuberculosis* complex in said sample or culture and wherein an absence of said PCR products indicates an absence of viable organisms of *M. tuberculosis* complex in said sample or culture.

6. The method of claim 5, wherein said first primer has a sequence shown in SEQ ID No. 13.

7. The method of claim 5, wherein said one or more additional primers having a sequence or sequences shown in SEQ ID No. 12, SEQ ID No. 14, or SEQ ID Nos. 12 & 14.

8. A method for detecting viable organisms of *M. tuberculosis* complex in a clinical sample or in vitro culture, comprising the steps of:
   isolating mRNA from said sample or culture;
   adding said isolated mRNA to a buffer containing a first primer, nucleotides and reverse transcriptase to form a first mixture;
   incubating said first mixture to permit synthesis of cDNA by said reverse transcriptase using said mRNA as template;
   adding an aliquot of said cDNA to a buffer containing one or more additional primers having a sequence or sequences shown in SEQ ID No. 12, SEQ ID No. 13, SEQ ID No. 14, SEQ ID Nos. 12 & 13 SEQ ID Nos. 12 & 14, SEQ ID No. 13 & 14, or SEQ ID Nos. 12–14, nucleotides and a DNA polymerase to form a second mixture;

incubating said second mixture through successive cycles of heating and cooling to facilitate synthesis of specific PCR products by said DNA polymerase;

detecting said PCR products using a specific detector primer having the sequence shown in SEQ ID No. 14, wherein a presence of said PCR products indicates a presence of viable organisms of *M. tuberculosis* complex in said sample or culture and wherein an absence of said PCR products indicates an absence of viable organisms of *M. tuberculosis* complex in said sample or culture.

9. The method of claim 8, wherein said first primer has a sequence selected from the group consisting of SEQ ID Nos. 12–14.

10. The method of claim 8, wherein said one or more additional primers having the sequence shown in SEQ ID No. 12.

11. The method of claim 8, wherein said one or more additional primers having the sequence shown in SEQ ID No. 12 and SEQ ID No. 14.

* * * * *

SEQUENCE LISTING

```
(1) GENERAL INFORMATION:

(iii) NUMBER OF SEQUENCES:  24

(2) INFORMATION FOR SEQ ID NO:1:

(i) SEQUENCE CHARACTERISTICS:
         (A) LENGTH:   40 bp
         (B) TYPE:  nucleic acid
         (C) STRANDEDNESS:  single-stranded
         (D) TOPOLOGY:  linear (ii) MOLECULE TYPE:
         (A) DESCRIPTION:  other nucleic acid (iii) HYPOTHETICAL:  no (iv) ANTI-SENSE:  no (v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:   1:

CGATTCCGCT CCAGACTTCT CGGGTTTGTC CGCCAACAGG                            40

(2) INFORMATION FOR SEQ ID NO:2:

(i) SEQUENCE CHARACTERISTICS:
         (A) LENGTH:   41 bp
         (B) TYPE:  nucleic acid
         (C) STRANDEDNESS:  single-stranded
         (D) TOPOLOGY:  linear (ii) MOLECULE TYPE:
         (A) DESCRIPTION:  other nucleic acid (iii) HYPOTHETICAL:  no (iv) ANTI-SENSE:  yes
```

(v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO: 2:

ACCGCATCGA GTACATGTCT CGGGTGACAA GCCGATTGCA G           41

(2) INFORMATION FOR SEQ ID NO:3:

(i) SEQUENCE CHARACTERISTICS:
      (A) LENGTH: 43 bp
      (B) TYPE: nucleic acid
      (C) STRANDEDNESS: single-stranded
      (D) TOPOLOGY: linear (ii) MOLECULE TYPE:
      (A) DESCRIPTION: other nucleic acid (iii) HYPOTHETICAL: no (iv) ANTI-SENSE: yes (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO: 3:

ACCGCATCGA GTACATGTCT CGGGTTTGAC AAGCCGATTG CAG         43

(2) INFORMATION FOR SEQ ID NO:4:

(i) SEQUENCE CHARACTERISTICS:
      (A) LENGTH: 18 bp
      (B) TYPE: nucleic acid
      (C) STRANDEDNESS: single-stranded
      (D) TOPOLOGY: linear (ii) MOLECULE TYPE:
      (A) DESCRIPTION: other nucleic acid (iii) HYPOTHETICAL: no (iv) ANTI-SENSE: no (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO: 4:

ACCTTCCTGA CCAGCGAG           18

(2) INFORMATION FOR SEQ ID NO:5:

(i) SEQUENCE CHARACTERISTICS:
                (A) LENGTH:  18 bp
                (B) TYPE:  nucleic acid
                (C) STRANDEDNESS:  single-stranded
                (D) TOPOLOGY:  linear (ii) MOLECULE TYPE:
                (A) DESCRIPTION:  other nucleic acid (iii) HYPOTHETICAL:  no (iv) ANTI-SENSE:  yes (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:   5:

AGATCATTGC CGACGAGC                                                       18

(2) INFORMATION FOR SEQ ID NO:6:

(i) SEQUENCE CHARACTERISTICS:
                (A) LENGTH:  16 bp
                (B) TYPE:  nucleic acid
                (C) STRANDEDNESS:  single-stranded
                (D) TOPOLOGY:  linear (ii) MOLECULE TYPE:
                (A) DESCRIPTION:  other nucleic acid (iii) HYPOTHETICAL:  no (iv) ANTI-SENSE:  yes (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:   6:

GCTGGGGGTG GTAGGC                                                         16

(2) INFORMATION FOR SEQ ID NO:7:

(i) SEQUENCE CHARACTERISTICS:
                (A) LENGTH:  14 bp
                (B) TYPE:  nucleic acid
                (C) STRANDEDNESS:  single-stranded
                (D) TOPOLOGY:  linear (ii) MOLECULE TYPE:
                (A) DESCRIPTION:  other nucleic acid (iii) HYPOTHETICAL:  no (iv) ANTI-SENSE:  yes (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:   7:

CCGACAGCGA GCCG                                                              14

(2) INFORMATION FOR SEQ ID NO:8:

(i) SEQUENCE CHARACTERISTICS:
           (A) LENGTH:  20 bp
           (B) TYPE:  nucleic acid
           (C) STRANDEDNESS:  single-stranded
           (D) TOPOLOGY:  linear (ii) MOLECULE TYPE:
           (A) DESCRIPTION:  other nucleic acid (iii) HYPOTHETICAL:  no (iv) ANTI-SENSE:  yes (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:   8:

CGCTGCCGGT GGGCTTCACG                                                        20

(2) INFORMATION FOR SEQ ID NO:9:

(i) SEQUENCE CHARACTERISTICS:
           (A) LENGTH:  13 bp
           (B) TYPE:  nucleic acid
           (C) STRANDEDNESS:  single-stranded
           (D) TOPOLOGY:  linear (ii) MOLECULE TYPE:
           (A) DESCRIPTION:  other nucleic acid (iii) HYPOTHETICAL:  no (iv) ANTI-SENSE:  yes (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:   9:

GCTTCACGGC CCT                                                               13

(2) INFORMATION FOR SEQ ID NO:10:

(i) SEQUENCE CHARACTERISTICS:
           (A) LENGTH:  12 bp
           (B) TYPE:  nucleic acid
           (C) STRANDEDNESS:  single-stranded
           (D) TOPOLOGY:  linear (ii) MOLECULE TYPE:
           (A) DESCRIPTION:  other nucleic acid (iii) HYPOTHETICAL: no (iv) ANTI-SENSE: yes (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:   10:

CGCTGCCGGT GG                                                              12

(2) INFORMATION FOR SEQ ID NO:11:

(i) SEQUENCE CHARACTERISTICS:
              (A) LENGTH:  21 bp
              (B) TYPE:  nucleic acid
              (C) STRANDEDNESS:  single-stranded
              (D) TOPOLOGY:  linear (ii) MOLECULE TYPE:
              (A) DESCRIPTION:  other nucleic acid (iii) HYPOTHETICAL: no (iv) ANTI-SENSE: yes (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:   11:

AGCTTGGGGA TCTGCTGCGT A                                                    21

(2) INFORMATION FOR SEQ ID NO:12:

(i) SEQUENCE CHARACTERISTICS:
              (A) LENGTH:  18 bp
              (B) TYPE:  nucleic acid
              (C) STRANDEDNESS:  single-stranded
              (D) TOPOLOGY:  linear (ii) MOLECULE TYPE:
              (A) DESCRIPTION:  other nucleic acid (iii) HYPOTHETICAL: no (iv) ANTI-SENSE: no (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:   12:

TCAGGGGATG GGGCCTAG                                                        18

(2) INFORMATION FOR SEQ ID NO:13:

(i) SEQUENCE CHARACTERISTICS:
        (A) LENGTH: 20 bp
        (B) TYPE: nucleic acid
        (C) STRANDEDNESS: single-stranded
        (D) TOPOLOGY: linear (ii) MOLECULE TYPE:
        (A) DESCRIPTION: other nucleic acid (iii) HYPOTHETICAL: no (iv) ANTI-SENSE: yes (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:   13:

GCTTGGGGAT CTGCTGCGTA                                        20

(2) INFORMATION FOR SEQ ID NO:14:

(i) SEQUENCE CHARACTERISTICS:
        (A) LENGTH: 23 bp
        (B) TYPE: nucleic acid
        (C) STRANDEDNESS: single-stranded
        (D) TOPOLOGY: linear (ii) MOLECULE TYPE:
        (A) DESCRIPTION: other nucleic acid (iii) HYPOTHETICAL: no (iv) ANTI-SENSE: no (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:   14:

TCGAGTGACC CGGCATGGGA GCG                                    23

(2) INFORMATION FOR SEQ ID NO:15:

(i) SEQUENCE CHARACTERISTICS:
        (A) LENGTH: 15 bp
        (B) TYPE: nucleic acid
        (C) STRANDEDNESS: single-stranded
        (D) TOPOLOGY: linear (ii) MOLECULE TYPE:
        (A) DESCRIPTION: other nucleic acid (iii) HYPOTHETICAL: no (iv) ANTI-SENSE: no (v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:   15:

TTGTCCGCCA ACAGG                                                         15

(2) INFORMATION FOR SEQ ID NO:16:

(i) SEQUENCE CHARACTERISTICS:
              (A) LENGTH:  16 bp
              (B) TYPE:  nucleic acid
              (C) STRANDEDNESS:  single-stranded
              (D) TOPOLOGY:  linear (ii) MOLECULE TYPE:
              (A) DESCRIPTION:  other nucleic acid (iii) HYPOTHETICAL:  no (iv) ANTI-SENSE:  yes (v) FRAGMENT TYPE:

(vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:   16:

GACAAGCCGA TTGCAG                                                        16

(2) INFORMATION FOR SEQ ID NO:17:

(i) SEQUENCE CHARACTERISTICS:
              (A) LENGTH:  16 bp
              (B) TYPE:  nucleic acid
              (C) STRANDEDNESS:  single-stranded
              (D) TOPOLOGY:  linear (ii) MOLECULE TYPE:
              (A) DESCRIPTION:  other nucleic acid (iii) HYPOTHETICAL:  no (iv) ANTI-SENSE:  yes (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:   17:

GACAAGCCGA TTGCAG                                                        16

(2) INFORMATION FOR SEQ ID NO:18:

(i) SEQUENCE CHARACTERISTICS:

(A) LENGTH: 19 bp
                (B) TYPE: nucleic acid
                (C) STRANDEDNESS: single-stranded
                (D) TOPOLOGY: linear (ii) MOLECULE TYPE:
                (A) DESCRIPTION: other nucleic acid (iii) HYPOTHETICAL: no (iv) ANTI-SENSE: no (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO: 18:

GCACGCCCAC CGGCAGCGC                                                 19

(2) INFORMATION FOR SEQ ID NO:19:

(i) SEQUENCE CHARACTERISTICS:
                (A) LENGTH: 22 bp
                (B) TYPE: nucleic acid
                (C) STRANDEDNESS: single-stranded
                (D) TOPOLOGY: linear (ii) MOLECULE TYPE:
                (A) DESCRIPTION: other nucleic acid (iii) HYPOTHETICAL: no (iv) ANTI-SENSE: yes (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO: 19:

TCACCCTGTT GGCGGACAAC CA                                             22

(2) INFORMATION FOR SEQ ID NO:20:

(i) SEQUENCE CHARACTERISTICS:
                (A) LENGTH: 13 bp
                (B) TYPE: nucleic acid
                (C) STRANDEDNESS: single-stranded
                (D) TOPOLOGY: linear (ii) MOLECULE TYPE:
                (A) DESCRIPTION: other nucleic acid (iii) HYPOTHETICAL: no (iv) ANTI-SENSE: yes (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO: 20:

GCGTGCTCAC CCT                                                              13

(2) INFORMATION FOR SEQ ID NO:21:

(i) SEQUENCE CHARACTERISTICS:
             (A) LENGTH: 23 bp
             (B) TYPE: nucleic acid
             (C) STRANDEDNESS: single-stranded
             (D) TOPOLOGY: linear (ii) MOLECULE TYPE:
             (A) DESCRIPTION: other nucleic acid (iii) HYPOTHETICAL: no (iv) ANTI-SENSE: yes (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:21:

CGCTGCCGGT GGGCGTGCTG CTC                                                   23

(2) INFORMATION FOR SEQ ID NO:22:

(i) SEQUENCE CHARACTERISTICS:
             (A) LENGTH: 109 bp
             (B) TYPE: nucleic acid
             (C) STRANDEDNESS: double-stranded
             (D) TOPOLOGY: linear (ii) MOLECULE TYPE:
             (A) DESCRIPTION: genomic DNA (iii) HYPOTHETICAL: no (iv) ANTI-SENSE: no (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO: 22:

ACCTTCCTGA CCAGCGAGCT GCCGCAATGG TTGTCCGCCA ACAGGGCCGT GAAGCCCACC           60

GGCAGCGCTG CAATCGGCTT GTCGATGGCC GGCTCGTCGG CAATGCTCT                      109

(2) INFORMATION FOR SEQ ID NO:23:

(i) SEQUENCE CHARACTERISTICS:
             (A) LENGTH: 109 bp
             (B) TYPE: nucleic acid
             (C) STRANDEDNESS: double-stranded
             (D) TOPOLOGY: linear (ii) MOLECULE TYPE:

```
        (A) DESCRIPTION:  genomic DNA (iii) HYPOTHETICAL:  no (iv) ANTI-SENSE:  no (vi) ORIGINAL SOURCE:

(vii) IMMEDIATE SOURCE:

(viii) POSITION IN GENOME:

(ix) FEATURE:

(x) PUBLICATION INFORMATION:

(xi) SEQUENCE DESCRIPTION:SEQ ID NO:   23:

ACCTTCCTGA CCAGCGAGCT GCCGCAATGG TTGTCCGCCA ACAGGGTGAG CACGCCCACC      60

GGCAGCGCTG CAATCGGCTT GTCGATGGCC GGCTCGTCGG CAATGCTCT               109

(2) INFORMATION FOR SEQ ID NO:24:

(i) SEQUENCE CHARACTERISTICS:
          (A) LENGTH:  978 bp
          (B) TYPE:  nucleic acid
          (C) STRANDEDNESS:  double-stranded
          (D) TOPOLOGY:  linear (ii) MOLECULE TYPE:
          (A) DESCRIPTION:  genomic DNA (iii) HYPOTHETICAL:  no (iv) ANTI-SENSE:  no (v) FRAGMENT TYPE:

(vi) ORIGINAL SOURCE:
          (A) ORGANISM:  Mycobacterium tuberculosis (vii) IMMEDIATE SOURCE:

(viii) POSITION IN GENOME:

(ix) FEATURE:
          (D) OTHER INFORMATION:  GenBank Accession Nos.:  M21839
              and X62398

(x) PUBLICATION INFORMATION:
          (A) AUTHORS:  De Wit, L
              Palou, M
              Content, J
          (B) TITLE:  Nucleotide Sequence of the 85B-Protein Gene of
              Mycobacterium bovis BCG and Mycobacterium tuberculosis
          (C) JOURNAL:  DNA Seq
          (D) VOLUME:  4
          (F) PAGES:  267-270
          (G) DATE:  1994

(xi) SEQUENCE DESCRIPTION:SEQ ID NO:   24:

ATGACAGACG TGAGCCGAAA GATTCGAGCT TGGGGACGCC GATTGATGAT CGGCACGGCA      60

GCGGCTGTAG TCCTTCCGGG CCTGGTGGGG CTTGCCGGCG GAGCGGCAAC CGCGGGCGCG     120

TTCTCCCGGC CGGGGCTGCC GGTCGAGTAC CTGCAGGTGC CGTCGCCGTC GATGGGCCGC     180

GACATCAAGG TTCAGTTCCA GAGCGGTGGG AACAACTCAC CTGCGGTTTA TCTGCTCGAC     240

GGCCTGCGCG CCCAAGACGA CTACAACGGC TGGGATATCA ACACCCCGGC GTTCGAGTGG     300

TACTACCAGT CGGGACTGTC GATAGTCATG CCGGTCGGCG GCAGTCCAG CTTCTACAGC      360

GACTGGTACA GCCCGGCCTG CGGTAAGGCT GGCTGCCAGA CTTACAAGTG GGAAACCTTC     420

CTGACCAGCG AGCTGCCGCA ATGGTTGTCC GCCAACAGGG CCGTGAAGCC CACCGGCAGC     480
```

```
GCTGCAATCG GCTTGTCGAT GGCCGGCTCG TCGGCAATGA TCTTGGCCGC CTACCACCCC    540

CAGCAGTTCA TCTACGCCGG CTCGCTGTCG GCCCTGCTGG ACCCCTCTCA GGGGATGGGG    600

CCTAGCCTGA TCGGCCTCGC GATGGGTGAC GCCGGCGGTT ACAAGGCCGC AGACATGTGG    660

GGTCCCTCGA GTGACCCGGC ATGGGAGCGC AACGACCCTA CGCAGCAGAT CCCCAAGCTG    720

GTCGCAAACA ACACCCGGCT ATGGGTTTAT TGCGGGAACG GCACCCCGAA CGAGTTGGGC    780

GGTGCCAACA TACCCGCCGA GTTCTTGGAG AACTTCGTTC GTAGCAGCAA CCTGAAGTTC    840

CAGGATGCGT ACAACGCCGC GGGCGGGCAC AACGCCGTGT TCAACTTCCC GCCCAACGGC    900

ACGCACAGCT GGGAGTACTG GGGCGCTCAG CTCAACGCCA TGAAGGGTGA CCTGCAGAGT    960

TCGTTAGGCG CCGGCTGA                                                 978
```